United States Patent
Yodfat et al.

(10) Patent No.: US 9,999,722 B2
(45) Date of Patent: Jun. 19, 2018

(54) PORTABLE MEDICAL FLUID DELIVERY DEVICE WITH DRIVE SCREW ARTICULATED WITH RESERVOIR PLUNGER

(75) Inventors: Ofer Yodfat, Modi'in (IL); Shai Ben-David, Ramat Ishai (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days. days.

(21) Appl. No.: 13/142,912

(22) PCT Filed: Dec. 30, 2009

(86) PCT No.: PCT/IL2009/001227
§ 371 (c)(1),
(2), (4) Date: Oct. 4, 2011

(87) PCT Pub. No.: WO2010/076792
PCT Pub. Date: Jul. 8, 2010

(65) Prior Publication Data
US 2012/0022453 A1 Jan. 26, 2012

Related U.S. Application Data

(60) Provisional application No. 61/166,816, filed on Apr. 6, 2009, provisional application No. 61/141,803, filed on Dec. 31, 2008.

(51) Int. Cl.
*A61M 5/145* (2006.01)
*A61M 5/142* (2006.01)
(Continued)

(52) U.S. Cl.
CPC .......... *A61M 5/1456* (2013.01); *A61M 5/142* (2013.01); *A61M 5/145* (2013.01);
(Continued)

(58) Field of Classification Search
CPC .... A61M 5/14248; A61M 2005/14268; A61M 5/142; A61M 5/145; A61M 5/1456;
(Continued)

(56) References Cited

U.S. PATENT DOCUMENTS 3,353,718 A * 11/1967 McLay ................. B01L 3/0224
222/158
4,498,843 A 2/1985 Schneider et al.
(Continued)

FOREIGN PATENT DOCUMENTS

EP 1776975 A2 4/2007
EP 1930037 B1 9/2010
(Continued)

OTHER PUBLICATIONS

International Search Report and Written Opinion of the International Search Authority for PCT Application No. PCT/IL2009/001227 dated May 20, 2010.

*Primary Examiner* — Nathan R Price
*Assistant Examiner* — Anh Bui
(74) *Attorney, Agent, or Firm* — Dinsmore & Shohl LLP

(57) ABSTRACT

A device for delivering fluid into the body is provided. The device may comprise a reservoir including at least one wall for retaining fluid and a plunger (400), wherein the plunger is articulated with a drive screw (300) having a distal end (304) that rotates within the plunger and displaces the plunger in a linear direction. The device may further comprise a reusable part having a motor, one or more gears and a receiving portion, and also a disposable part having a reservoir, a plunger and a drive screw having a proximal end capable of engaging with the receiving portion upon connecting the reusable part and the disposable part

21 Claims, 12 Drawing Sheets

(51) Int. Cl.
*A61M 5/14* (2006.01)
*A61M 5/315* (2006.01)
(52) U.S. Cl.
CPC ...... *A61M 5/1452* (2013.01); *A61M 5/14244* (2013.01); *A61M 5/14248* (2013.01); *A61M 5/31515* (2013.01); *A61M 5/1413* (2013.01); *A61M 5/31513* (2013.01); *A61M 2005/14268* (2013.01); *A61M 2005/14506* (2013.01); *A61M 2005/14533* (2013.01); *A61M 2005/14573* (2013.01)
(58) Field of Classification Search
CPC ............ A61M 5/14566; A61M 5/1452; A61M 5/14244; A61M 2005/14506; A61M 2005/14573; A61M 2005/14533
USPC .......................................... 604/67, 131, 155
See application file for complete search history.

(56) References Cited

U.S. PATENT DOCUMENTS

| | | | | |
|---|---|---|---|---|
| 5,183,466 | A * | 2/1993 | Movern | A61M 5/5013 604/110 |
| 5,928,202 | A * | 7/1999 | Linnebjerg | 604/228 |
| 5,957,895 | A | 9/1999 | Sage et al. | |
| 6,120,479 | A * | 9/2000 | Campbell | A61M 5/5013 604/110 |
| 6,248,093 | B1 | 6/2001 | Moberg | |
| 6,485,461 | B1 | 11/2002 | Mason et al. | |
| 6,589,229 | B1 | 7/2003 | Connelly et al. | |
| 6,723,072 | B2 | 4/2004 | Flaherty et al. | |
| 6,740,059 | B2 | 5/2004 | Flaherty | |
| 7,390,314 | B2 * | 6/2008 | Stutz et al. | 604/155 |
| 2003/0009133 | A1 * | 1/2003 | Ramey | A61M 5/1456 604/155 |
| 2003/0120219 | A1 | 6/2003 | Nielsen et al. | |
| 2005/0051580 | A1 * | 3/2005 | Ramey | 222/390 |
| 2005/0238507 | A1 | 10/2005 | Dilanni et al. | |
| 2006/0270987 | A1 * | 11/2006 | Peter | A61M 5/14244 604/151 |
| 2007/0106218 | A1 * | 5/2007 | Yodfat et al. | 604/131 |
| 2007/0191702 | A1 | 8/2007 | Yodfat et al. | |
| 2008/0077081 | A1 * | 3/2008 | Mounce et al. | 604/67 |
| 2008/0097327 | A1 * | 4/2008 | Bente | A61J 1/1406 604/155 |
| 2008/0097381 | A1 * | 4/2008 | Moberg | A61M 5/1413 604/506 |
| 2008/0214916 | A1 | 9/2008 | Yodfat et al. | |
| 2008/0215035 | A1 | 9/2008 | Yodfat et al. | |
| 2008/0319414 | A1 | 12/2008 | Yodfat et al. | |
| 2009/0133691 | A1 * | 5/2009 | Yamada | A61M 11/041 128/200.16 |
| 2009/0259198 | A1 * | 10/2009 | Chong | A61B 5/14532 604/221 |
| 2010/0217230 | A1 | 8/2010 | Yodfat et al. | |
| 2010/0292651 | A1 * | 11/2010 | Yodfat | A61M 5/1413 604/189 |
| 2011/0160652 | A1 * | 6/2011 | Yodfat | A61M 5/1413 604/66 |
| 2011/0221583 | A1 * | 9/2011 | Yodfat | A61M 5/14248 340/384.6 |
| 2012/0053522 | A1 * | 3/2012 | Yodfat | A61M 5/1413 604/151 |

FOREIGN PATENT DOCUMENTS

| | | |
|---|---|---|
| GB | 1031950 | 6/1966 |
| WO | WO 2007/052277 A1 | 5/2007 |
| WO | WO 2008/094833 A1 | 8/2007 |
| WO | WO 2008/012817 A1 | 1/2008 |
| WO | WO 2008/078318 A2 | 7/2008 |
| WO | WO 2008/078319 A1 | 7/2008 |
| WO | WO 2008/127345 A1 | 10/2008 |
| WO | WO 2008/139458 A2 | 11/2008 |
| WO | WO 2009/001346 A1 | 12/2008 |
| WO | WO 2009/013736 A1 | 1/2009 |
| WO | WO 2009/016636 A2 | 2/2009 |
| WO | WO 2009/125398 A2 | 10/2009 |

* cited by examiner

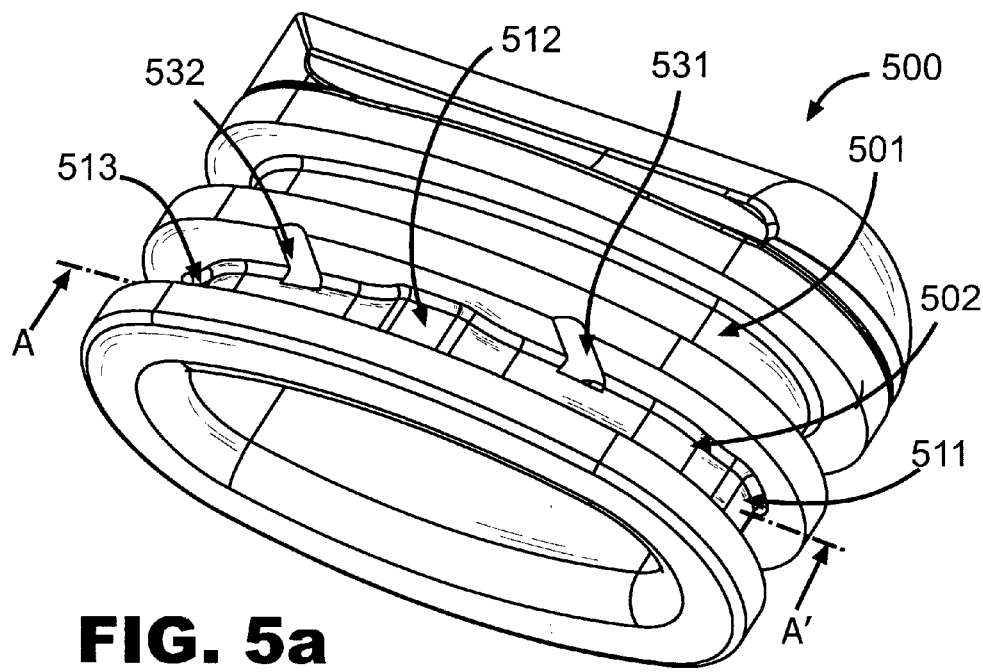
FIG. 5a
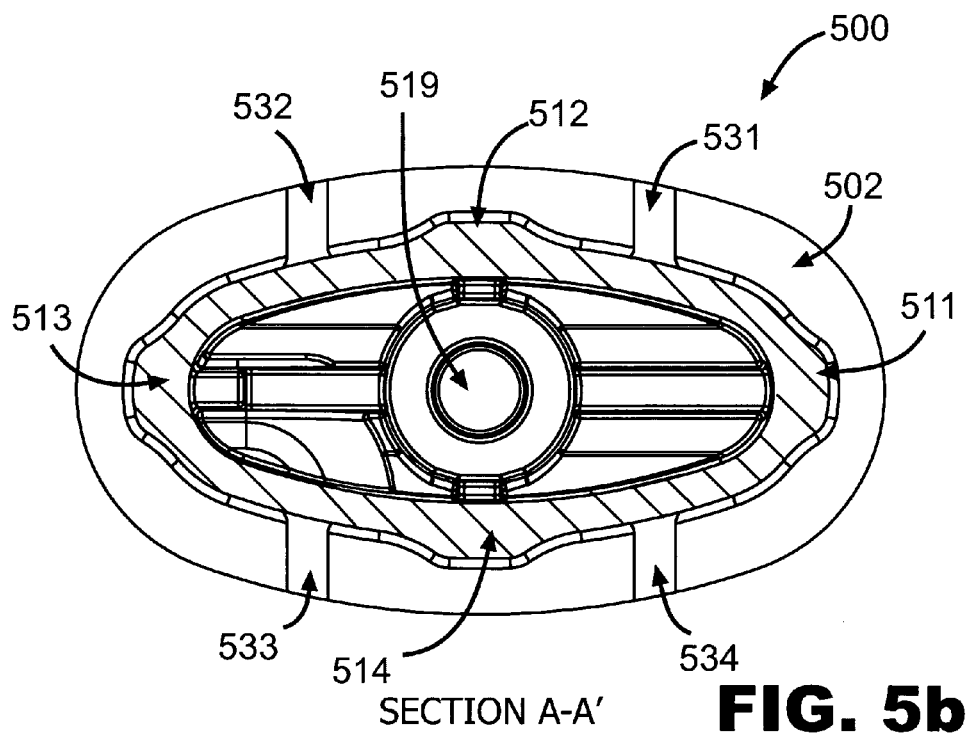
SECTION A-A'  FIG. 5b

SECTION B-B'

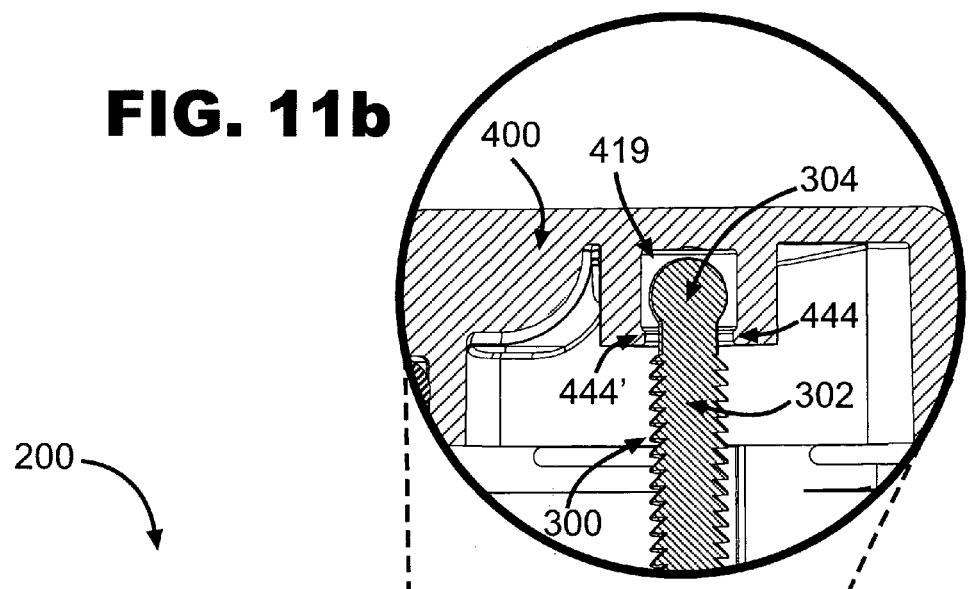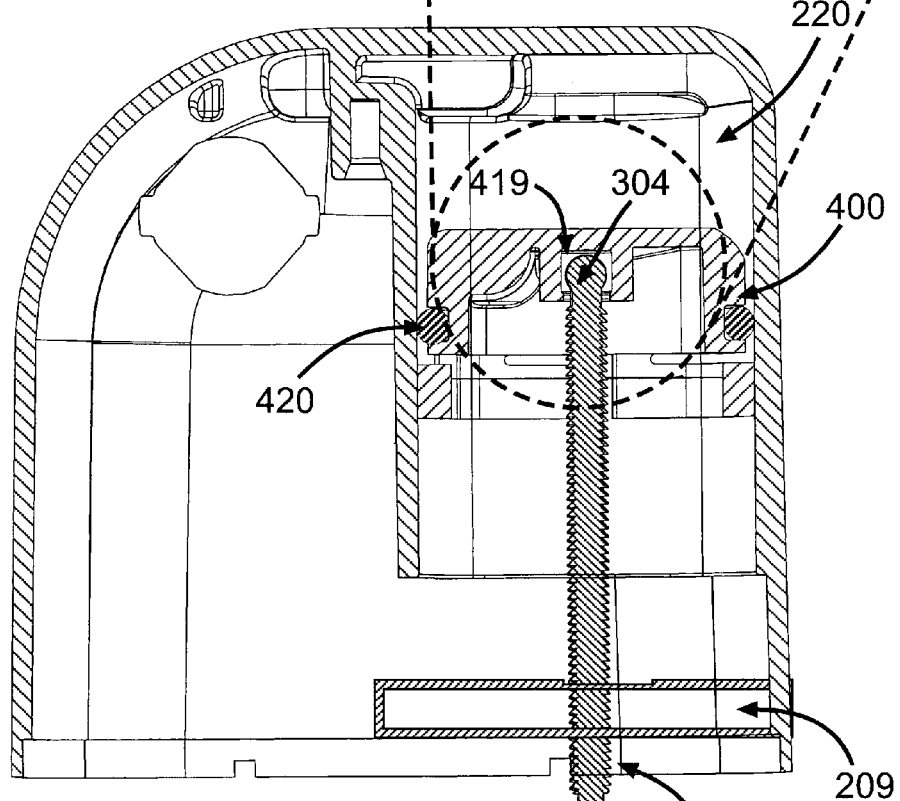

PORTABLE MEDICAL FLUID DELIVERY DEVICE WITH DRIVE SCREW ARTICULATED WITH RESERVOIR PLUNGER

CROSS-REFERENCE TO RELATED APPLICATIONS

The present application is a 35 U.S.C. § 371 national stage entry of PCT/IL2009/001227, which has an international filing date of Dec. 30, 2009 and claims priority to U.S. Provisional Patent Application Nos. 61/141,803, filed on Dec. 31, 2008 and entitled "Device and Method for Accurate Fluid Delivery" and U.S. Provisional Patent Application No. 61/166,816, filed on Apr. 6, 2009 and entitled "Device and Method for Accurate Fluid Delivery," the disclosures of which are incorporated herein by reference in their entireties.

FIELD

Devices and methods for accurate delivery of fluid into the body are provided. In particular, devices that include a dispensing unit having a reusable part and a disposable part are provided. More particularly, a two-part skin-securable unit having a pumping mechanism for delivering fluid at a high accuracy rate is provided.

BACKGROUND

Medical treatment of many illnesses requires continuous drug infusion into various parts of the body via subcutaneous and/or intravenous injections. Diabetes mellitus patients, for example, require the administration of varying amounts of insulin throughout the day to control their blood glucose levels. In recent years, ambulatory portable insulin infusion pumps have emerged as a superior alternative to multiple daily syringe injections of insulin for Type 1 and Type 2 diabetes patients. These pumps, which deliver insulin at a continuous basal rate, as well as in bolus volumes, were developed to liberate patients from repeated self-administered injections, and allow them to maintain a near-normal daily routine. Both basal and bolus volumes must be delivered in precise doses, according to individual prescription, since an overdose or underdose of insulin could be fatal.

The first generation of portable insulin pumps refers to a "pager-like" device with a reservoir contained within a housing. The reservoir is typically a barrel-shaped, syringe-like component which enables the delivery of medicine by a continuous forward motion of a plunger into the reservoir. Examples of such devices are disclosed in U.S. Pat. Nos. 6,248,093 and 7,390,314. In conventional configurations, a motor rotates a gear, which in turn rotates a threaded drive screw. The plunger has a proximal end that contains gaskets and an elongated member shaped like a cylinder which is internally threaded for engagement with the drive screw. As a result, the motor rotates the drive screw which engages the threads of the cylinder and converts the rotation of the drive screw into a linear motion to displace the plunger in an axial direction. These first generation devices represent a significant improvement over multiple daily injections, but suffer major drawbacks, including large size, heavy weight, and long tubing.

To avoid these drawbacks, a new concept was proposed and implemented in second generation pumps. The new concept concerns a remote-controlled, skin-adherable device having a bottom surface adapted to be in contact with a patient's skin. A reservoir is contained within the housing and filled using an additional syringe to draw medicine from a vial with an injection needle into the reservoir. This concept is discussed in U.S. Pat. Nos. 4,498,843, 5,957,895, 6,589,229, 6,740,059, 6,723,072, and 6,485,461. These second generation devices still have several drawbacks, the most significant being that the entire device should be disposed every 2-3 days (due to insertion site infections and reduced insulin absorption), including all the expensive components, such as electronics and the driving mechanism.

A typical driving mechanism of a second generation device is described in U.S. Patent Application Publ. No. 2005/0238507 assigned to Insulet Corporation. In this device, a plunger is rigidly connected to a non-rotating threaded drive screw and also coupled to a drive wheel that includes a thread-engaging mechanism that moves from a non-thread-engaging position to a thread-engaging position. The non-thread-engaging position allows the threaded drive screw to pass freely through the drive wheel when the reservoir is being filled. The thread-engaging position allows the threaded drive screw to be advanced when the drive wheel is rotated.

A third generation of pumps was devised to avoid the cost issues associated with second generation pumps and to expand patient customization. Examples of such devices are described in co-owned, co-pending U.S. patent application Ser. No. 11/397,115 (Publication No. 2007/0106218), filed on Apr. 3, 2006 and entitled "Systems and Methods for Sustained Medical Infusion and Devices Related Thereto," and co-owned International Patent Application No. PCT/IL06/001276 (Publication No. WO/2007/052277), filed on Nov. 5, 2006 and entitled "Modular Portable Infusion Pump," the disclosures of, which are incorporated herein by reference in their entireties. These third generation devices contain a remote control unit and a skin-securable (e.g., adherable) dispensing unit having two parts: (1) a reusable part containing electronics, at least a portion of the driving mechanism and other relatively expensive components, and (2) a disposable part containing the reservoir and other less expensive components. Other third generation devices are also disclosed in co-owned, co-pending U.S. patent application Ser. No. 11/989,681, filed on Jan. 28, 2008, and co-owned International Patent Application No. PCT/IL07/000932 (Publication No. WO/2008/012817), filed on Jul. 24, 2007, both entitled "Systems, Devices, and Methods for Fluid/Drug Delivery," the disclosures of which are incorporated herein by reference in their entireties.

A typical driving mechanism of third generation devices is described in U.S. Patent Application Publ. No. 2008/0097327 assigned to Medtronic MiniMed. This device has a disposable part that includes a plunger having a rigidly-connected drive screw. The device also has a reusable part that contains a motor and a gear that comprises a drive wheel. Upon connection of the reusable part and disposable part, the drive screw is engaged with the drive wheel. Rotation of the drive wheel is converted to linear motion of the drive screw.

A fourth generation of pumps was devised as dispensing units that can be disconnected and reconnected to a skin-securable (e.g., adherable) cradle unit and can also be operated by buttons located on the reusable part. Examples of fourth generation devices are disclosed in co-owned, co-pending U.S. patent application Ser. No. 12/004,837 (Publication No. 2008/0215035) and co-owned International Patent Application No. PCT/IL07/001578 (Publication No. WO2008/078318), both filed on Dec. 20, 2007 and entitled "Systems, Devices, and Methods for Sustained Delivery of a Therapeutic Fluid," the disclosures of which are incorporated herein by reference in their entireties. Other fourth generation devices are also disclosed in co-owned, co-pending International Patent Application No. PCT/IL08/001001 (Publication No. WO2008/078318), filed on Jul. 20, 2008 and entitled "Manually Operable Portable Infusion Pump," and co-owned, co-pending International Patent Application No. PCT/IL08/001057 (Publication No. WO2009/016636), filed on Jul. 31, 2008 and entitled "Portable Infusion Device Provided with Means for Monitoring and Controlling Fluid Delivery," the disclosures of which are incorporated herein by reference in their entireties.

Third and fourth generation devices may be incorporated with an analyte (e.g., glucose) sensing apparatus that enables continuous readings of analyte levels. Based on these analyte readings, fluid may then be automatically (i.e., a closed-loop system) dispensed or semi-automatically (i.e., an open-loop system) dispensed, should the user wish to control delivery. Fourth generation sensing and dispensing devices are disclosed in co-owned, co-pending U.S. patent application Ser. No. 11/706,606 (Publication No. 2007/0191702), filed on Feb. 14, 2007 and entitled "Systems and Methods for Sensing Analyte and Dispensing Therapeutic Fluid," in co-owned, co-pending U.S. patent application Ser. No. 11/963,481 (Publication No. 2008/0214916), filed on Dec. 21, 2007 and entitled "Fluid Delivery with In Vivo Electrochemical Analyte Sensing," and in co-owned International Patent Application No. PCT/IL2007/001579 (Publication No. WO2008/078319), filed on Dec. 20, 2007 and entitled "Fluid Delivery with In Vivo Electrochemical Analyte Sensing," the disclosures of all of which are incorporated herein by reference in their entireties.

Third and fourth generation devices may also be two-part (e.g., a disposable part and a reusable part) skin-securable (e.g., adherable) devices having a "syringe-type" pumping mechanism. Here, a plunger slides within the reservoir to urge fluid (e.g., insulin) out of the reservoir. The plunger may be moved forward by a rotating drive screw that has a distal end coupled with the plunger. Linear motion may be achieved by rotation of the drive screw within a non-rotating drive nut disposed in the disposable part of the device. Rotation of the drive screw within the non-rotating drive nut causes linear motion of the drive screw relative to the drive nut. In such devices, the drive screw may also be used as a handle for pulling the plunger out of the reservoir for reservoir filling. After filling, the disposable part is connected to the reusable part, thereby engaging the drive screw with the driving mechanism in the reusable part of the device.

One major limitation of this design concerns the misalignment and/or eccentricity of the drive screw during the forward motion of the plunger within the reservoir. In particular, manufacturing and/or assembly tolerances of the driving mechanism may result in eccentric rotation of the drive screw within the device and/or the engagement of the proximal end of the drive screw with the driving mechanism may become misaligned and cause such eccentric rotation of the drive screw. This eccentric rotation of the drive screw is transferred to the plunger during the plunger's forward motion within the reservoir and creates plunger wobbling within the reservoir. This wobbling results in mechanical inefficiencies within the device and causes inaccuracies in the amount and rate of fluid delivery to the body.

SUMMARY

Device and method embodiments that deliver fluid into the body at highly accurate rates are described herein. In some embodiments, the fluid is insulin. Some embodiments provide for devices that deliver fluid into the body that include a reservoir, a plunger configured for insertion and movement in the reservoir, and a drive screw having a distal end and being articulated with the plunger, wherein the drive screw displaces the plunger in a linear direction upon being rotated. In some embodiments, the plunger may move in a linear direction within the reservoir in a manner similar to a "syringe-type" mechanism when a drive screw is rotated.

In some embodiments, the reservoir may include at least one wall for retaining the fluid to be delivered. In some embodiments, the reservoir may comprise a non-circular cross-section. Accordingly, the cross-section of at least a portion of the plunger may substantially correspond to the non-circular cross-section of the reservoir in some embodiments. The device may also comprise one or more housings accommodating the reservoir, the plunger and the drive screw. According to some embodiments, at least a portion of the one or more housings comprises at least a portion of the at least one wall of the reservoir.

In some embodiments, the plunger may have one or more grooves to support one or more gaskets. At least one of the grooves may include one or more projections that cause a gasket supported by the at least one groove having the one or more projections to contact the at least one wall of the reservoir via those portions of the gasket that are positioned over the one or more projections, according to some embodiments. In some embodiments, the plunger may have one or more guide flaps that contact the at least one wall of the reservoir. In some plunger embodiments, at least a portion of one or more of the guide flaps may be resilient. In some embodiments, the drive screw may be articulated with the plunger via engagement of the distal end of the drive screw with a socket contained within the plunger. Some embodiments of the distal end of the drive screw may comprise a substantially spherical shape.

In some embodiments, the socket of the plunger may comprise a longitudinal cross-section selected from the group consisting of polygonal, circular and any combination thereof. In some embodiments, the socket of the plunger may comprise a transverse cross-section selected from the group consisting of polygonal, circular and any combination thereof. In some embodiments, the articulation of the distal end of the drive screw with the socket of the plunger may provide for angular movement of the drive screw relative to the plunger. The socket of the plunger may also include one or more protrusions for securing the drive screw to the plunger upon engagement of the distal end of the drive screw with the socket, according to some embodiments. Engagement of the distal end of the drive screw with the socket, in some embodiments, may comprise a snap-fit engagement. Furthermore, articulation of the distal end of the drive screw with the socket may be configured to enable pushing of the plunger using the drive screw, pulling of the plunger using the drive screw and/or substantially unrestricted rotation of the distal end within the socket.

In some embodiments, the drive screw may have a distal end that is articulated with the plunger and a proximal end that engages with a receiving component (e.g., a rotating sleeve) and/or with one or more gears connected to a motor. The drive screw may be at least partially threaded, according to some embodiments. The drive screw, in some embodiments, may be articulated with the plunger via engagement of the distal end of the drive screw with a socket contained within the plunger. In some device embodiments, the distal end of the drive screw has a round shape and the socket has a longitudinal cross-section selected from the group consisting of quadrangular, pentagonal, trapezoidal, triangular, circular, oval and any combination thereof. The socket may correspond to the shape of the distal end of the drive screw. In some embodiments, the articulation of the distal end of the drive screw with the socket of the plunger provides for angular movement of the drive screw relative to the plunger.

Some device embodiments may include an engagement member configured for coupling with the drive screw and having a threaded portion and a non-threaded portion, wherein when the drive screw is coupled to the non-threaded portion of the engagement member, the drive screw is capable of linearly moving substantially unrestricted, and when the drive screw is coupled to the threaded portion of the engagement member, the drive screw is capable of linearly moving upon rotation of the drive screw. In some embodiments, the engagement member may comprise a drive nut. In some embodiments, the drive nut may comprise a threaded opening and a non-threaded opening, wherein when the drive nut is positioned in a first position, the drive screw is placed in the non-threaded opening and is configured to linearly move substantially unrestricted, and when the drive nut is positioned in a second position, the drive screw is placed in the threaded opening and is configured to linearly move upon rotation of the drive screw. Upon connection of the reusable part and the disposable part, the drive nut may be displaced from the first position to the second position, according to some embodiments.

Some device embodiments may be configured as a two-piece unit with a reusable part having a motor, one or more gears and a receiving portion configured for mechanical connection with the one or more gears, as well as a disposable part having a reservoir, a plunger and a drive screw with a proximal end and a distal end, wherein the proximal end is capable of engaging with the receiving portion upon connection of the reusable part and the disposable part. Upon connecting the disposable part and the reusable part, rotation of the receiving portion may result in rotation of the drive screw via engagement of the proximal end with the receiving portion, according to some embodiments. In some embodiments, the disposable part may further comprise an engagement member configured for coupling with the drive screw and having a threaded portion and a non-threaded portion, wherein when the drive screw is coupled to the non-threaded portion of the engagement member, the drive screw is capable of linearly moving substantially unrestricted, and when the drive screw is coupled to the threaded portion of the engagement member, the drive screw is capable of linearly moving upon rotation of the drive screw. Some embodiments of the engagement member may be configured as a drive nut.

In certain embodiments, the device may further include a sensor for monitoring and/or detecting analyte levels in the body. In some embodiments, the analyte is glucose. The device may be configured to deliver fluid to the body based on the detected analyte levels, according to some embodiments.

In some embodiments, the device may comprise a cradle unit securable to the skin of the user, wherein one or more housings of the device are removably connectable to the cradle unit. In some embodiments, the device may comprise a remote control for at least one of initiating fluid delivery, programming the device, acquiring data and communicating with other electronic devices.

Some device embodiments may comprise a dispensing unit, a skin-securable (e.g., adherable) cradle unit ("cradle") and a remote control unit ("remote control"). In some embodiments, the dispensing unit may be disconnected from and reconnected to the cradle unit. In some embodiments, a connecting lumen may be used to provide fluid communication between the dispensing unit and a subcutaneous cannula that is rigidly connected to the cradle unit. Fluid delivery may be controlled remotely using one or more buttons and/or switches (e.g., a push-button switch) positioned on the remote control or locally by positioning one or more buttons and/or switches (e.g., a push-button switch) directly on the dispensing unit.

Embodiments of the dispensing unit may include a pumping mechanism, a reservoir and an outlet port. The dispensing unit may be configured as a single-piece unit including a reservoir, a power source, electronic components, and a pumping mechanism or as a two-piece unit having a reusable part, which may contain a motor, one or more gears, a receiving portion (e.g., a rotating sleeve), electronic components, and other relatively expensive components, and a disposable part, which may contain an outlet port, a reservoir, a plunger, a drive screw, and a drive nut. In some embodiments, the disposable part and/or the reusable part may contain the power source (e.g., batteries). In some embodiments, the reservoir may have a low profile (e.g., oval, ellipse, or four or eight arches) to provide a thin configuration of the dispensing unit. In some embodiments, the reusable part and disposable part may each have an external housing (e.g., shell) and an internal structure (e.g., chassis). In some embodiments, when the reusable part and disposable part are connected, the reusable part and disposable part external housings and internal structures are coupled together and cause the drive nut to move from a disengaged position to an engaged position so as to engage with threads located on the drive screw. Furthermore, upon connection of the reusable part and the disposable part, the proximal end of the drive screw may become engaged with the receiving portion located within the reusable part, according to some embodiments.

In some embodiments, the cradle unit may be configured as a flat sheet with an adhesive surface, a passageway for a subcutaneous cannula, and snaps for securing a cannula and the dispensing unit. In some embodiments, the remote control may be configured as a handheld device for programming fluid infusion rates, controlling the dispensing unit, acquiring data, and providing visual, audible and/or vibratory notifications. In some embodiments, the remote control may be configured, without limitation, as a wristwatch, a cellular phone, a personal digital assistance, iPhone, iPod, an mp3 player or a personal computer.

Methods aspects of the present invention may include a method for delivering fluid into the body by articulating a distal end of a drive screw of a fluid delivery device with a plunger of the fluid delivery device and rotating the drive screw relative to a drive nut of the fluid delivery device to advance the plunger into a reservoir of the fluid delivery device, wherein the articulation between the distal end of the drive screw and the plunger of the fluid delivery device provides for angular movement of the drive screw relative to the plunger.

Embodiments of the method may include one or more of the above described features of the device, as well as any of the following features.

In some method embodiments, the fluid delivery device may comprise a reusable part having a motor, one or more gears and a receiving portion driven by at least one of the motor and the one or more gears, as well as a disposable part having a reservoir, a plunger, a drive nut and a drive screw with a proximal end and a distal end articulated with the plunger, wherein upon connection of the reusable part and the disposable part, the proximal end of the drive screw is engaged with the receiving portion. Upon connection of the reusable part and the disposable part, rotation of the receiving portion may result in rotation of the drive screw via engagement of the proximal end of the drive screw with the receiving portion, according to some embodiments. Some method embodiments may include connecting the reusable part and the disposable part. Some method embodiments may include rotating the receiving portion of the reusable part of the device.

In some embodiments, the drive nut of the fluid delivery device may comprise a threaded opening and a non-threaded opening, wherein when the drive nut is positioned in a first position, the drive screw is placed in the non-threaded opening and is configured to linearly move substantially unrestricted, and when the drive nut is positioned in a second position, the drive screw is placed in the threaded opening and is configured to linearly move upon rotation of the drive screw. Some method embodiments may include displacing the drive nut from the first position to the second position. In some embodiments, connecting the reusable part and the disposable part may result in displacement of the drive nut from the first position to the second position. In some embodiments, the drive screw may be articulated with the plunger via engagement of the distal end of the drive screw with a socket contained within the plunger. In some method embodiments, the articulation of the distal end of the drive screw with the socket of the plunger provides the angular movement of the drive screw relative to the plunger. Furthermore, the socket may comprise a longitudinal cross-section selected from the group consisting of polygonal, circular and any combination thereof and a transverse cross-section selected from the group consisting of polygonal, circular and any combination thereof. In some embodiments, the distal end of the drive screw comprises a substantially spherical shape.

Accordingly, it is an object of at least some of the embodiments to provide a device for delivering fluids into the body that includes a "syringe-type" pumping mechanism having a reservoir and a plunger, wherein the plunger may have a socket articulated with the distal end of a drive screw to prevent the plunger from wobbling when the proximal end of the drive screw is misaligned or eccentric relative to the driving mechanism (e.g., the gears and/or motor) of the device.

It is another object of at least some of the embodiments to provide a device for delivering fluid into the body that includes a "syringe-type" pumping mechanism having a reservoir and a plunger with one or more grooves that support one or more gaskets therein. In some embodiments, at least two grooves may be provided to support at least two gaskets. In certain embodiments, at least one groove may be configured such that the gasket supported by that one groove is entirely pressed against the inner walls of the reservoir so as to provide stability and also prevent fluid leakage from the reservoir. In some embodiments, at least one groove may be configured such that the gasket supported by that one groove is not entirely pressed against the inner walls of the reservoir and instead has limited contact therewith so as to provide enhanced stability to reduce plunger wobbling as the plunger advances within the reservoir while also reducing the friction between the gasket and the inner walls of the reservoir.

It is another object of at least some of the embodiments to provide a device for delivering fluid into the body that includes a "syringe-type" pumping mechanism having a reservoir and a plunger with a single groove to support a single gasket to prevent fluid leakage from the reservoir and one or more guide flaps for reducing plunger wobbling as the plunger advances within the reservoir while also reducing friction between the plunger and the inner walls of the reservoir.

It is also an object of at least some of the embodiments to provide a method for delivering fluid into the body at a high rate of accuracy, wherein the method includes articulating a distal end of a drive screw of a fluid delivery device with a plunger of the device such that the articulation between the distal end of the drive screw and the plunger provides for angular movement between the drive screw and the plunger. In some embodiments, the drive screw may be rotated to advance the plunger into a reservoir of the device and urge fluid into the body. It is another object of at least some of the embodiments to provide a dispensing unit for sustained delivery of fluid with a controlled rate of injection of the fluid into the body.

It is another object of at least some of the embodiments to provide a dispensing unit that is thin, has no external tubing and can be secured to any part of the body.

It is another object of at least some of the embodiments to provide a fluid delivery device that contains a skin-securable (e.g., adherable) cradle unit with a passageway for a sub-cutaneous cannula and snaps for removably securing the dispensing unit.

It is another object of at least some of the embodiments to provide a device that includes a skin-securable (e.g., adherable) dispensing unit having a "syringe-type" pumping mechanism for delivering fluid at a high accuracy rate.

It is also an object of at least some of the embodiments to provide a device that includes a skin-securable (e.g., adherable) dispensing unit that continuously monitors analyte (e.g., glucose) levels in the body (e.g., in the blood or in interstitial fluid) and delivers fluid (e.g., insulin) according to the detected analyte levels in the body via an automatic (i.e., a closed-loop) or semi-automatic (i.e., a open-loop) system.

It is another object of at least some of the embodiments to provide a dispensing unit, wherein infusion programming can be carried out remotely using one or more buttons and/or switches (e.g., a push-button switch) positioned on a remote control unit or locally using one or more buttons and/or switches (e.g., a push-button switch) positioned directly on the dispensing unit.

It is another object of at least some of the embodiments to provide a device for delivering fluid into a patient's body through a flexible, soft subcutaneously-insertable cannula.

It is another object of at least some of the embodiments to provide a skin-securable (e.g., adherable) dispensing unit that is miniature, discreet, economical for the users and highly cost-effective. The dispensing unit may include a "syringe-type" pumping mechanism that includes a reservoir and a plunger that delivers fluid at a high accuracy rate.

BRIEF DESCRIPTION OF THE DRAWINGS

FIGS. 5a-5b and 6a-6d show various embodiments of a plunger.

FIGS. 11a-11b show a longitudinal cross-section view of the disposable part of a two-piece dispensing unit having a reservoir, a plunger, a drive screw, and a drive nut, according to some embodiments.

DETAILED DESCRIPTION

This detailed description presents device and method embodiments for accurate delivery of fluid into the body according to the foregoing objectives and summary. Some device embodiments may include a piston-type pumping mechanism having a plunger movable within a fluid reservoir. According to at least some embodiments, the plunger may have a proximal end containing a socket (also referred to as "cavity") for receiving and articulating with a distal end of a rotatable drive screw. The connection between the socket and the drive screw may be configured to prevent the plunger from wobbling during rotation of the drive screw when the drive screw is misaligned or eccentric and, in turn, deliver fluid at a high rate of accuracy.

Figure 1:
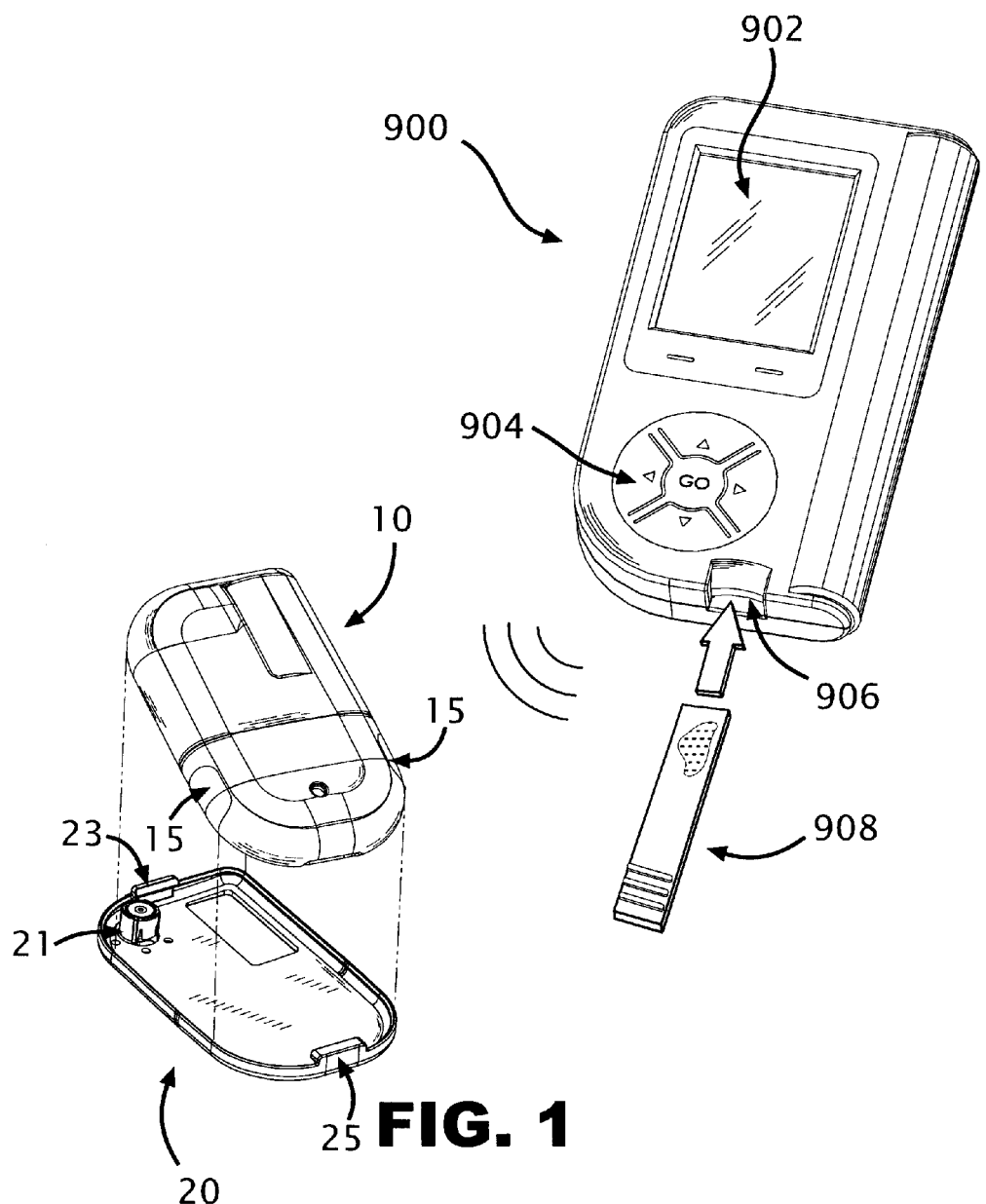
FIG. 1 shows a device for delivering fluid into the body that includes a remote control containing an integrated blood glucose monitor, a two-part dispensing unit, and a skin-securable cradle unit, according to some embodiments.

FIG. 1 shows an embodiment of a device for delivering fluid into the body that includes a dispensing unit ("unit") 10, cradle unit ("cradle") 20 and remote control 900. In some embodiments, the unit 10 may be referred to as a patch unit due to its structural similarity to a thin patch that can be affixed to the body of a patient. Depending on the embodiment, the unit 10 may be a single-piece unit or a two-piece unit and, furthermore, may be configured to disconnect from and reconnect to the cradle 20. In some embodiments, delivery of fluid may be initiated using one or more buttons and/or switches 15 (e.g., a push-button switch) located on the unit 10, either as an alternative to a remote control, or as backup to the remote control 900 when the remote control 900 is not at hand, for example, as disclosed in co-owned, co-pending International Patent Application No. PCT/IL08/001001 (Publication No. WO2008/078318), filed on Jul. 20, 2008 and entitled "Manually Operable Portable Infusion Pump," and co-owned, co-pending International Patent Application No. PCT/IL08/001057 (Publication No. WO2009/016636), filed on Jul. 31, 2008 and entitled "Portable Infusion Device Provided with Means for Monitoring and Controlling Fluid Delivery," the disclosures of which are incorporated herein by reference in their entireties. In some embodiments, the one or more buttons and/or switches 15 may include one or more bolus buttons or switches, such as a push-button switch, for triggering the delivery of a bolus volume of fluid (e.g., insulin) into the body. Embodiments of the remote control 900 may include an integrated analyte sensor (e.g., a blood glucose monitor), a screen/display 902, a keypad 904, and a slot 906 to receive a blood test strip 908. The remote control 900 may also be used to program the unit 10, acquire data from a patient, and communicate with other electronic devices (e.g., computers) to carry out, for example, data downloading and uploading. The remote control 900 may be configured, without limitation, as a wrist-watch, a cellular phone, a personal digital assistance, an mp3 player, iPod, iPhone or a personal computer. Embodiments of the cradle unit 20 may be configured as a substantially flat sheet having a surface that is securable (e.g., adherable) to the skin of a patient, e.g., via an adhesive layer provided on a bottom surface of the cradle 20. The cradle 20 may also contain a passageway for insertion of a cannula into the body. In some embodiments, the passageway of cradle 20 may be defined by a well 21 configured as a protrusion (e.g., a tubular protrusion) extending upwardly from a surface of the cradle 20. The well 21 may comprise connectors (e.g., snaps or latches) to secure the cannula (not shown) to the cradle 20. The cradle 20 may further include one or more connectors 23, 25 (e.g., snaps, latches) to secure the unit 10 to the cradle 20. Insertion of the cannula may be carried out manually or via a dedicated inserter, as described, for example, in co-owned, co-pending U.S. patent application Ser. No. 12/215,255 (Publication No. 2008/0319414), filed on Jun. 25, 2008 and entitled "Insertion Device" and co-owned, co-pending International Patent Application No. PCT/IL08/000860 (Publication No. WO/2009/001346), filed on Jun. 25, 2008 and entitled "A Cannula-Insertion Device," the disclosures of which are incorporated herein by reference in their entireties.

Examples of the device shown in FIG. 1 are disclosed in co-owned, co-pending U.S patent application Ser. No. 12/004,837 (Publication No. 2008/0215035) and co-owned International Patent Application No. PCT/IL07/001578 (Publication No. WO2008/078318), both filed on Dec. 20, 2007 and entitled "Systems, Devices, and Methods for Sustained Delivery of a Therapeutic Fluid," the disclosures of which are incorporated herein by reference in their entireties. Device examples are also disclosed in co-owned, co-pending U.S. patent application Ser. No. 11/397,115 (Publication No. 2007/0106218), filed on Apr. 3, 2006 and entitled "Systems and Methods for Sustained Medical Infusion and Devices Related Thereto," in co-owned International Patent Application No. PCT/IL06/001276 (Publication No. WO/2007/052277), filed on Nov. 5, 2006 and entitled "Modular Portable Infusion Pump," and in co-owned International Patent Application No. PCT/IL09/000388 (Publication No. WO/2009/125398), filed on Apr. 7, 2009 and entitled "Systems, Devices and Methods for Fluid Delivery," the disclosures of all of which are incorporated herein by reference in their entireties.

Furthermore, co-owned, co-pending U.S. patent application Ser. No. 11/706,606 (Publication No. 2007/0191702), filed on Feb. 14, 2007 and entitled "Systems and Methods for Sensing Analyte and Dispensing Therapeutic Fluid" and U.S. patent application Ser. No. 11/963,481 (Publication No. 2008/0214916), filed on Dec. 21, 2007 and entitled "Fluid Delivery with In Vivo Electrochemical Analyte Sensing," as well as co-owned International Patent Application No. PCT/IL07/001579 (Publication No. WO2008/078319), filed on Dec. 20, 2007 and entitled "Fluid Delivery with In Vivo Electrochemical Analyte Sensing," the disclosures of all of which are incorporated herein by reference in their entireties, disclose devices that include a dispensing unit (e.g., an insulin dispensing patch unit) and an analyte sensor (e.g., a continuous glucose monitor). Such dual-function devices have a similar configuration to the device shown in FIG. 1 and described above and thus may also be disconnected from and reconnected to the body at a patient's discretion. In some dual-function device embodiments, fluid may be dispensed according to readings of blood glucose levels in the body taken by the analyte sensor. Based on these readings, fluid may be automatically (i.e., a closed-loop system) dispensed or semi-automatically (i.e., an open-loop system) dispensed should the user wish to control fluid delivery. In certain embodiments of semi-automatic dispensing, input from the user (e.g., meal times, changes in basal insulin delivery rates, or boluses before meals), as well as input from the analyte sensor itself, may be used within a specific algorithm to determine the amount of fluid to be delivered by the device.

Figure 2:
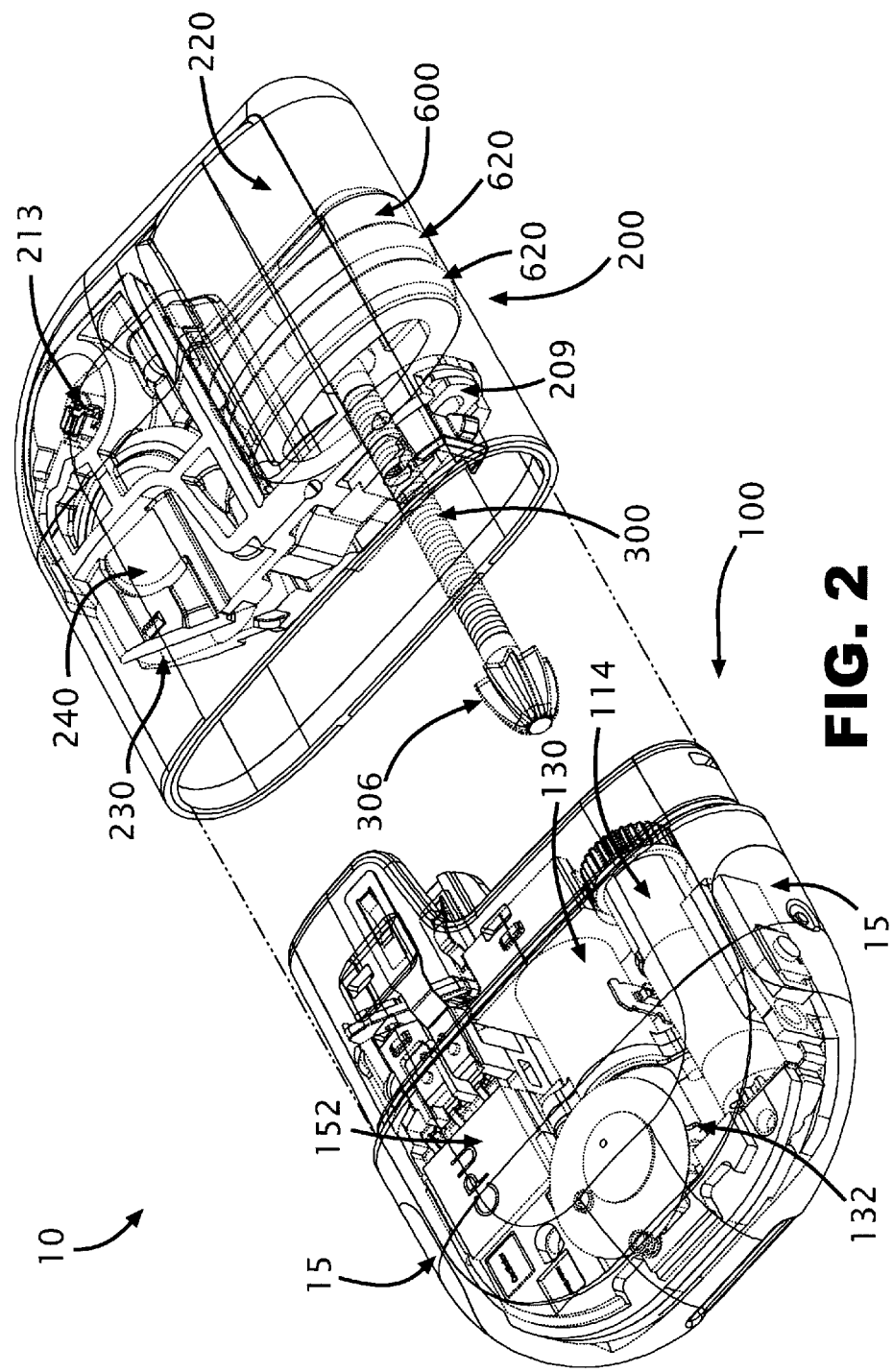
FIG. 2 shows a two-part dispensing unit having a reusable part and a disposable part, according to some embodiments.

FIG. 2 shows one embodiment of the dispensing unit 10 having two parts—a reusable part 100 and a disposable part 200. The reusable part 100 and the disposable part 200 may each have external housings and internal structures. The internal structures are used as a skeletal frame for support and attachment of at least some of the components contained at least partially within the external housings of the reusable part 100 and the disposable part 200. The unit 10 may have a pumping mechanism. In some embodiments, the pumping mechanism may be a "syringe-type" mechanism and include a plunger 600 configured to fit and move within a reservoir 220. According to some embodiments, the reusable part 100 may contain relatively expensive components, including without limitation, a motor 132, one or more gears 130, a rotating sleeve 114, electronic components including one, or more controllers or processors (e.g., CPU or MCU) 152, and one or more buttons and/or switches 15 for initiating fluid delivery. Depending on the embodiment, the motor 132 may be without limitation a DC motor, a stepper motor, or a shape memory alloy ("SMA") motor and the one or more gears 130 may be without limitation external gears, internal gears, spur gears, helical gears, bevel gears or any combination thereof. The one or more gears 130 may be arranged in the form of a planetary gear system. According to some embodiments, the disposable part 200 may include a reservoir 220, a plunger 600 having one or more gaskets 620, a threaded drive screw 300 (also referred to as "threaded plunger rod" or "plunger rod") having a distal end (not shown) articulated with the plunger 600 and a proximal end 306 receivable within the rotating sleeve 114 (also referred to as "receiving portion" or "receiving component"), a drive nut 209 (also referred to as "screw nut"), and an outlet port 213. Some embodiments of the unit 10 may contain a power source 240 (e.g., one or more batteries of any suitable type, including AA, AAA or button-type) that may be located in the disposable part 200 or in the reusable part 100 or partially in both when the two parts are connected. The outlet port 213 may contain a connecting lumen (not shown) that maintains fluid communication between the reservoir 220 and the body of the patient via a cannula (not shown). A delivery tube 230 may be used in certain embodiments to connect the reservoir 220 to the connecting lumen (not shown). According to some embodiments, forward motion of the plunger 600 will urge fluid (e.g., insulin) from the reservoir 220 and into the delivery tube 230. The cross-section of the reservoir 220 may be circular. In some embodiments, the cross-section of the reservoir 220 may be non-circular, e.g., oval, elliptical, or include a plurality of arches (e.g., four or eight arches), to provide a low profile of the unit 10, as disclosed, for example, in co-owned International Patent Application No. PCT/IL08/000641 (Publication No. WO/2008/139458), filed on May 11, 2008 and entitled "A Positive Displacement Pump," the disclosure of which is incorporated herein by reference in its entirety. The cross-section of at least a portion of the plunger 600 may be circular, oval, elliptical or include a plurality of arches, depending on the reservoir embodiment. A portion of the external housing and/or internal structure of the disposable part 200 may serve as one or more walls of the reservoir 220 or the reservoir 220 may be a separate component contained within the disposable part 200, depending on the embodiment.

Figure 3:
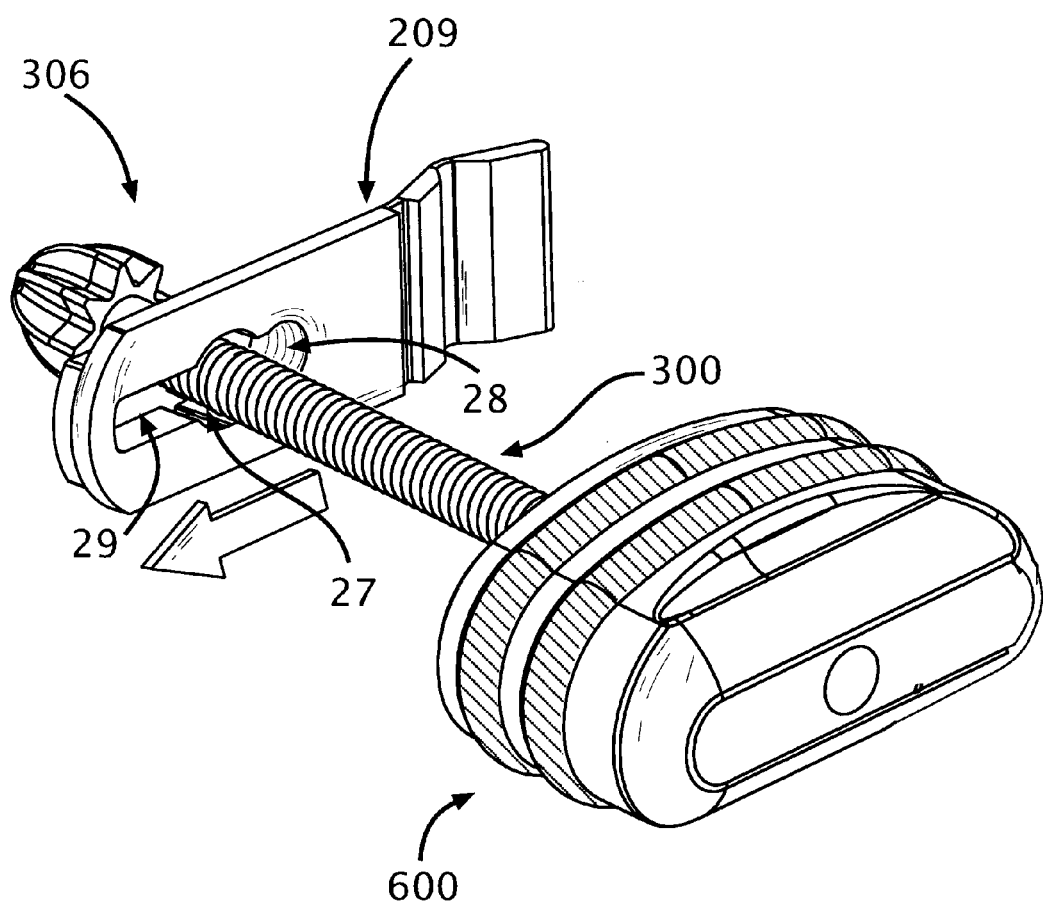
FIG. 3 shows an assembly of a plunger, drive screw and drive nut, according to some embodiments.

FIG. 3 shows an embodiment of the plunger 600, drive screw 300 and drive nut 209 assembly, where threaded engagement between the drive screw 300 and the drive nut 209 is utilized. In some embodiments, the drive nut 209 may include two conjugated openings or slots—a non-threaded slot 27 and a threaded slot 28. The threaded slot 28 may include inner threads traversing at least a portion of its circumference. Before the reusable part 100 and the disposable part 200 are connected, the drive screw 300 may be positioned in the non-threaded slot 27 and freely movable forward and backward therein. This position is useful for filling the reservoir 220 by using the drive screw 300 to pull the plunger 600 outwardly within the reservoir 220 such that fluid is drawn into the reservoir through the exit port 213. According to some embodiments, when the reusable part 100 and the disposable part 200 are connected, the drive nut 209 is forced to slide in a lateral direction (see arrow in FIG. 3), causing the drive screw 300 to engage with the threaded slot 28, as described, for example, in co-owned, co-pending International Patent Application No. PCT/IL09/000388 (Publication No. WO/2009/125398), filed on Apr. 7, 2009 and entitled "Systems, Devices and Methods for Fluid Delivery," the disclosure of which is incorporated herein by reference in its entirety. In some embodiments, the drive nut 209 may include at least one additional opening or slot 29, to provide the drive nut 209 with elasticity and prevent irreversible deformation of the drive nut 209 during engagement. Some embodiments of the additional slot 29 may be conjugated with the non-threaded slot 27 and the threaded slot 28. Also upon connection of the reusable part 100 and the disposable part 200, the proximal end 306 may engage with the rotating sleeve 114 of the driving mechanism (see FIG. 2). The one or more gears 130 may rotate due to their coupling with the motor 132. As a result, the drive screw 300 is rotated due to the engagement between the rotating sleeve 114, which is driven by the one or more gears 130, and the proximal end 306 of the drive screw 300. On the other hand, the drive nut 209 may be held substantially stationary within the disposable part 200 and thus when the drive screw 300 rotates, the threaded engagement between the drive screw 300 and the threaded slot 28 causes the drive screw 300 (and the plunger 600 coupled to the distal end of the drive screw 300) to be displaced linearly within the reservoir 220. As a result of this displacement, fluid is urged out of the reservoir 220 and into the delivery tube 230, according to some embodiments. As can be understood by one having ordinary skill in the art, the assembly described in FIG. 3, as well as other plunger and/or drive screw embodiments disclosed hereinafter, may be employed in dispensing units connectable to a cradle unit, as shown in FIG. 1 above, as well as in dispensing units capable of direct attachment to the patient's skin, e.g., using an adhesive layer provided at a bottom surface of the dispensing unit, and in "pager-type" devices that deliver fluid into the patient's body using an infusion set.

Figure 4:
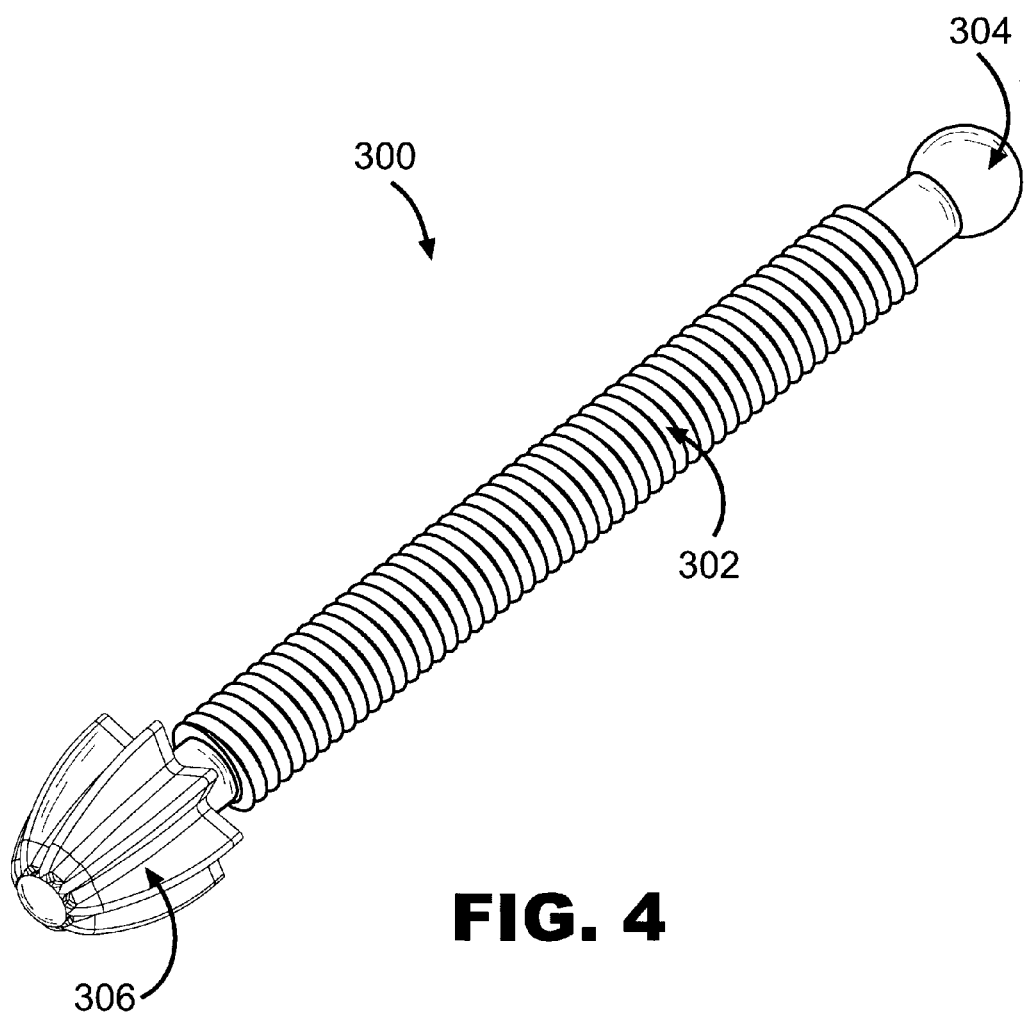
FIG. 4 shows an embodiment of a drive screw.

As shown in FIG. 4, some embodiments of the drive screw 300 may include a shaft 302 (also referred to as "body portion" or "elongated body portion"), at least a part of which may be threaded, a proximal end 306 and a distal end 304. In some embodiments, the proximal end 306 may engage with the rotating sleeve 114 when the reusable part 100 and the disposable part 200 are connected and rotate when the rotating sleeve 114 is rotated. The distal end 304 may be round in shape and configured to articulate with the plunger 600. It is noted that one of ordinary skill in the art will appreciate that a perfectly round (i.e., spherical) distal end 304 is not always achievable during the manufacturing process and may include one or more flat portions. The term "distal end" used hereinafter includes a spherical distal end, a semi-spherical distal end (e.g., a distal end configured as a truncated sphere), as well as any shape or configuration known to one of ordinary skill in the art that is capable of allowing the drive screw to articulate with and rotate relative to the plunger.

FIGS. 5a-6d show various configurations of the plunger of the present disclosure according to some embodiments. As shown in these configurations, the plunger may have a substantially oval shape. In turn, the reservoir will have a corresponding substantially oval shape as well. Other plunger shapes may include without limitation round, elliptical, arched or barrel-shaped (e.g., 4 or 8 arches). The plunger may be manufactured from, without limitation, flexible (e.g., rubber) and/or polymeric (e.g., polypropylene) materials, and may include one or more metal portions, for example, within its socket for improved durability of the interface between the socket and the distal end 304 of the drive screw 300. In some embodiments, the plunger may have one or more grooves for supporting one or more gaskets.

FIG. 5a shows a plunger 500 having two grooves 501 and 502 for supporting two gaskets (not shown). According to some embodiments, first groove 501 may have a uniform depth and be configured such that the entire outer circumference of the gasket supported by the first groove 501 maintains constant contact with the inner walls of the reservoir 220 to stabilize the plunger 500 within the reservoir 220 and prevent fluid leakage from the reservoir 220. Second groove 502 may have a non-uniform depth and, in some embodiments, include one or more projections (e.g., projections 511, 512 and 513 shown in FIG. 5a), so that the gasket supported by the second groove 502 contacts the inner walls of the reservoir 220 via those portions of the gasket positioned over projections 511, 512 and 513. This second gasket (i.e., the gasket supported by the second groove 502) provides enhanced stabilization of the plunger 500 within the reservoir 220 and reduces plunger wobbling as the plunger 500 is advanced in the reservoir 220. Moreover, reducing the contact area between the second gasket and the inner walls of the reservoir 220 by having specific portions of the second gasket contact the inner walls reduces the friction between the plunger 500 and the reservoir 220 and, in turn, reduces the amount of force required to displace the plunger 500 within the reservoir 220. This configuration of the second groove 502 also enables penetration of gases into and out of the space between the two gaskets during a sterilization process of the disposable part 200 and thus ensures that the disposable part 200 is entirely sterilized. In some embodiments, penetration of gases into and out of the space between the two gaskets is further achieved by providing the plunger 500 with one or more apertures between the two gaskets (e.g., apertures 531 and 532 shown in FIG. 5a). In some embodiments, the second groove 502 is configured to be similar to the first groove 501, i.e., it has a uniform depth and is configured such that the entire outer circumference of the gasket supported by the second groove 502 maintains constant contact with the inner walls of the reservoir 220. In this case, both gaskets may prevent fluid leakage from the reservoir 220 in addition to stabilizing the plunger 500 within the reservoir 220.

FIG. 5b is a cross-sectional view of the plunger 500 taken along the line A-A' shown in FIG. 5a. FIG. 5b shows projections 511, 512, 513 and 514, apertures 531, 532, 533 and 534 and a socket 519 configured to receive and engage with the distal end 304 of the drive screw 300 for articulation between the drive screw 300 and the plunger 500. The number of projections, their shape and their location along the second groove 502 may vary depending on the embodiment. The projections 511, 512, 513 and 514 shown in FIG. 5b may be shaped to efficiently stabilize the plunger 500 within the reservoir 220 while also minimizing the contact area between the gasket supported by the second groove 502 and the inner walls of the reservoir 220. In addition, the projections may be dispersed along the second groove 502 to achieve proper positioning and orientation of the plunger 500 within the reservoir 220. For example, one embodiment of an oval-shaped plunger may include at least four projections symmetrically dispersed along the second groove 502. In another embodiment, a round-shaped plunger may include three or more equally-spaced projections. In some embodiments, both grooves 501 and 502 may have uniform depth and at least one of the two gaskets supported by first groove 501 and second groove 502 may be configured to have non-uniform thickness, such that the non-uniform gasket has a limited number of contact points with the inner walls of the reservoir 220.

In some embodiments, the plunger of the present disclosure may have a single groove to support a single gasket and have in addition one or more projections/protrusions, manufactured, at least in part, from a flexible material (e.g., rubber), to further stabilize the plunger within the reservoir 220. Disposition of the one or more projections/protrusions may be done using, for example, over-molding or double-injection processes.

Figure 6A:
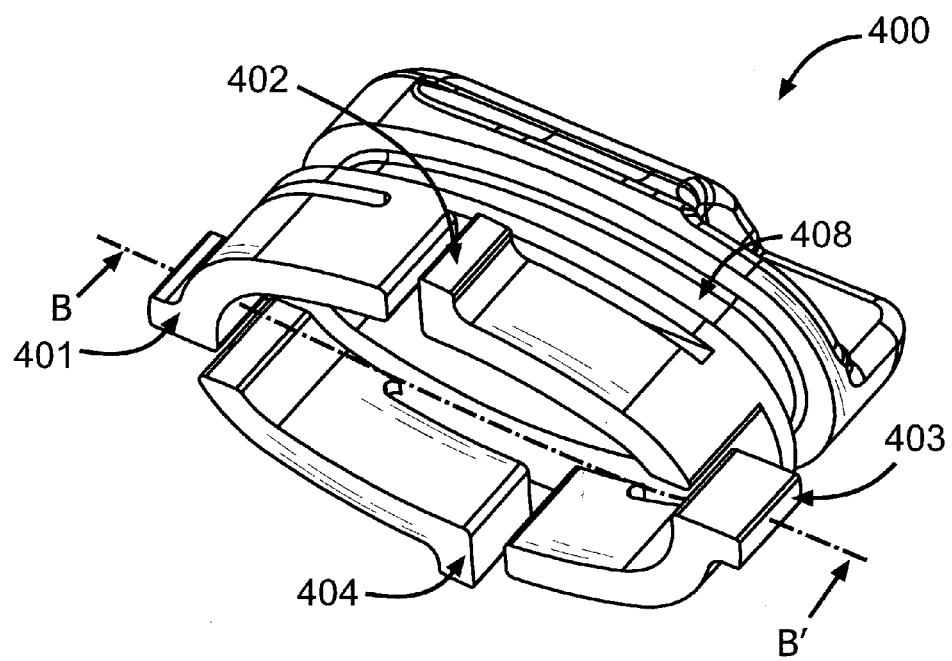

FIG. 6a shows a plunger 400 having a single groove 408 that supports a single gasket (not shown), and four guide flaps 401, 402, 403 and 404 that support the plunger 400 within the reservoir 220 and serve to reduce plunger wobbling when the plunger 400 is advanced in the reservoir 220. The number of guide flaps may vary depending on the embodiment. In some embodiments, at least a portion of each guide flap may maintain contact with the inner walls of the reservoir 220 as the plunger 400 is advanced within the reservoir 220. The guide flaps 401, 402, 403 and 404 may be configured to ensure that at least a portion of each guide flap 401, 402, 403 and 404 maintains contact with the inner walls of the reservoir 220. In some embodiments, the guide flaps 401, 402, 403 and 404 may be separate from each other so that the positioning and orientation of each guide flap 401, 402, 403 and 404 relative to the inner walls of the reservoir 220 can be adjusted individually, or with minimal correlation to the positioning and orientation of any of the other guide flaps relative to the inner walls of the reservoir 220. In addition, each guide flap 401, 402, 403 and 404 may be configured as an elongated segment, which may be at least partially curved, extending from the plunger 400 at a single contact point, to provide the guide flap 401, 402, 403 and 404 with elasticity.

Figure 6B:
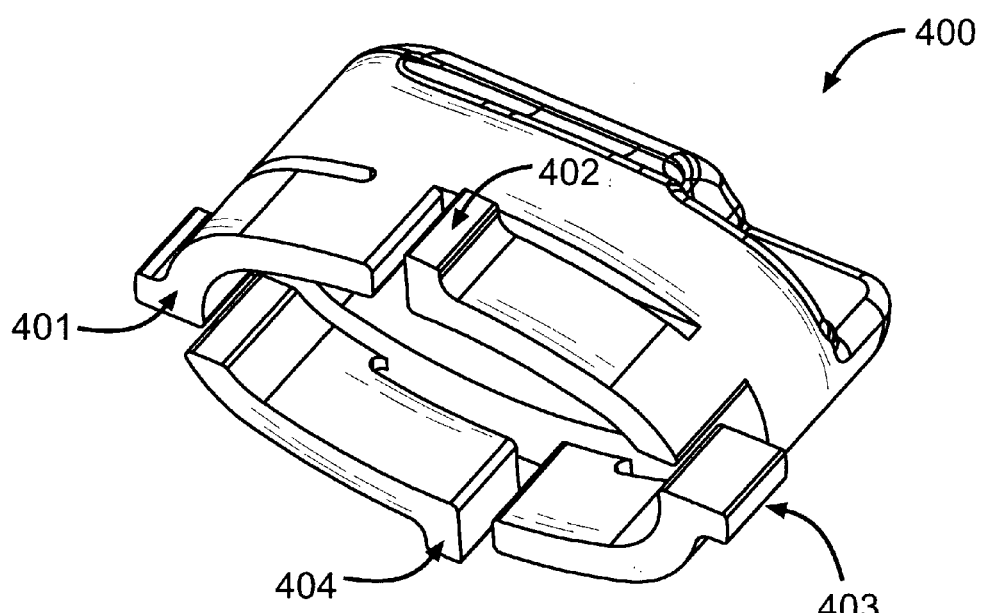
Figure 6C:
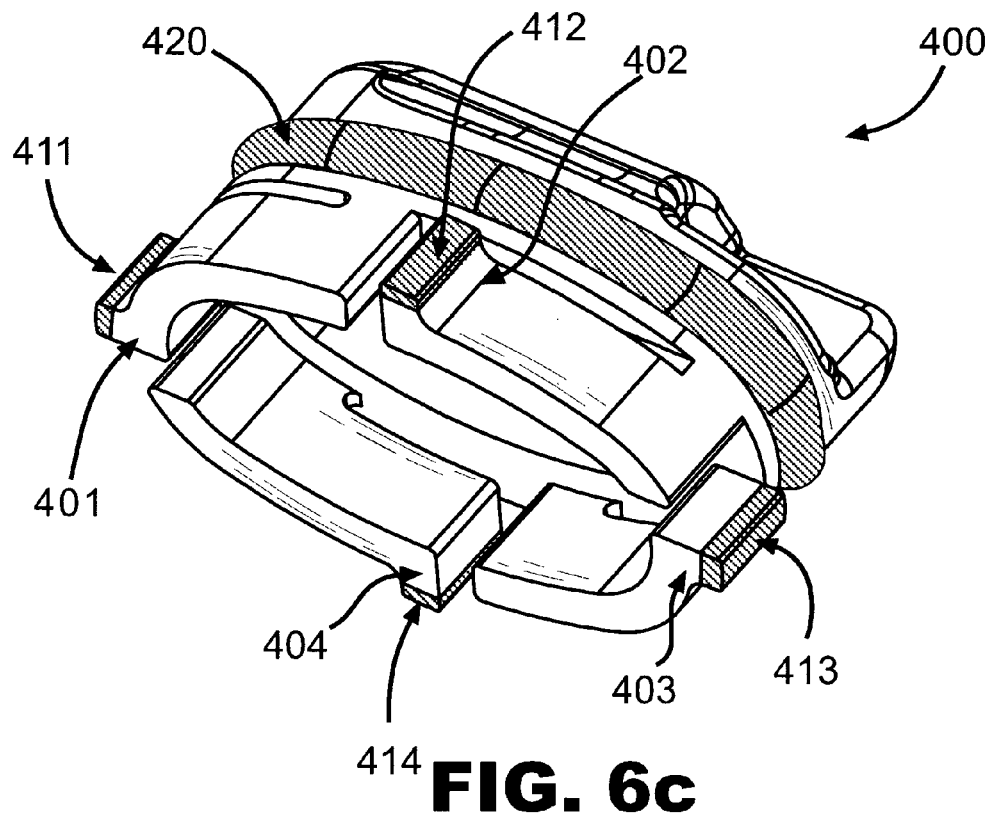
Figure 6D:
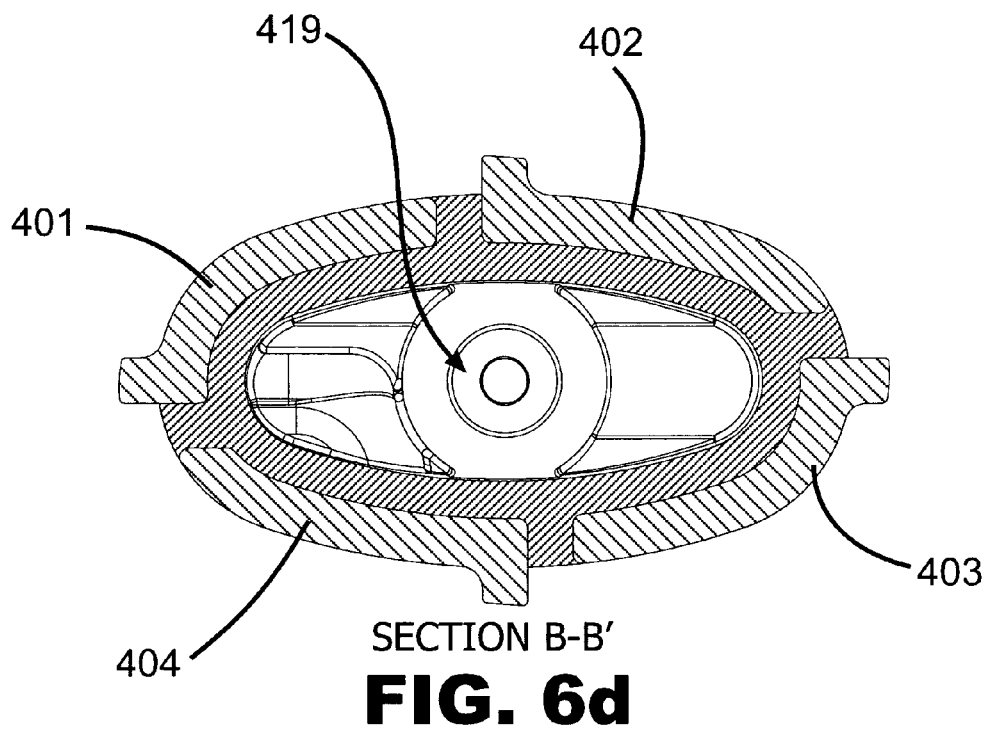

FIG. 6b shows the plunger 400 without one or more grooves and gaskets and having four guide flaps 401, 402, 403 and 404. FIG. 6c shows the plunger 400 with a gasket 420 and four guide flaps 401, 402, 403 and 404 having flexible material (e.g., sponge or rubber) at their ends 411, 412, 413 and 414, respectively, to reduce friction forces when the plunger 400 is advanced in the reservoir 220 and provide further support to prevent plunger wobbling. FIG. 6d shows a transverse cross-sectional view of the plunger 400 taken along the line B-B' shown in FIG. 6a. FIG. 6d shows four guide flaps 401, 402, 403 and 404 and a socket 419 configured to receive and engage the distal end 304 of the drive screw 300 for articulation between the drive screw 300 and the plunger 400.

Figure 7:
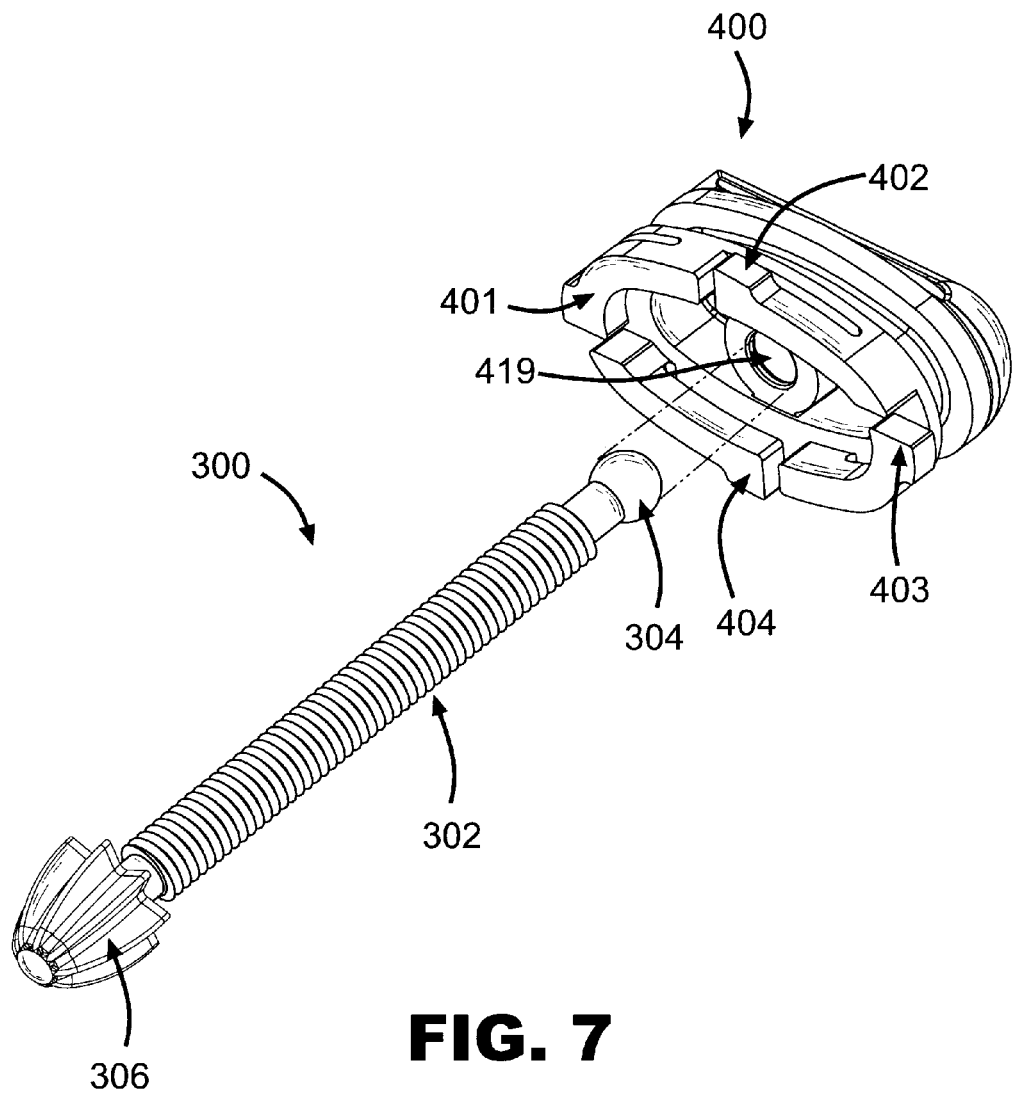
FIG. 7 shows an embodiment of a plunger and a drive screw before articulation.

FIG. 7 shows embodiments of both the plunger 400 and the drive screw 300 before the two components are engaged for articulation. The proximal end of the plunger 400 is shown as having four guide flaps 401, 402, 403 and 404 and a socket 419 for articulation with the distal end 304 (e.g., a spherical distal end) of the drive screw 300. In some embodiments, such as the one depicted in FIG. 7, the drive screw 300 may have a shaft 302, at least a portion of which may be threaded, a proximal end 306 and a distal end 304.

Figure 8:
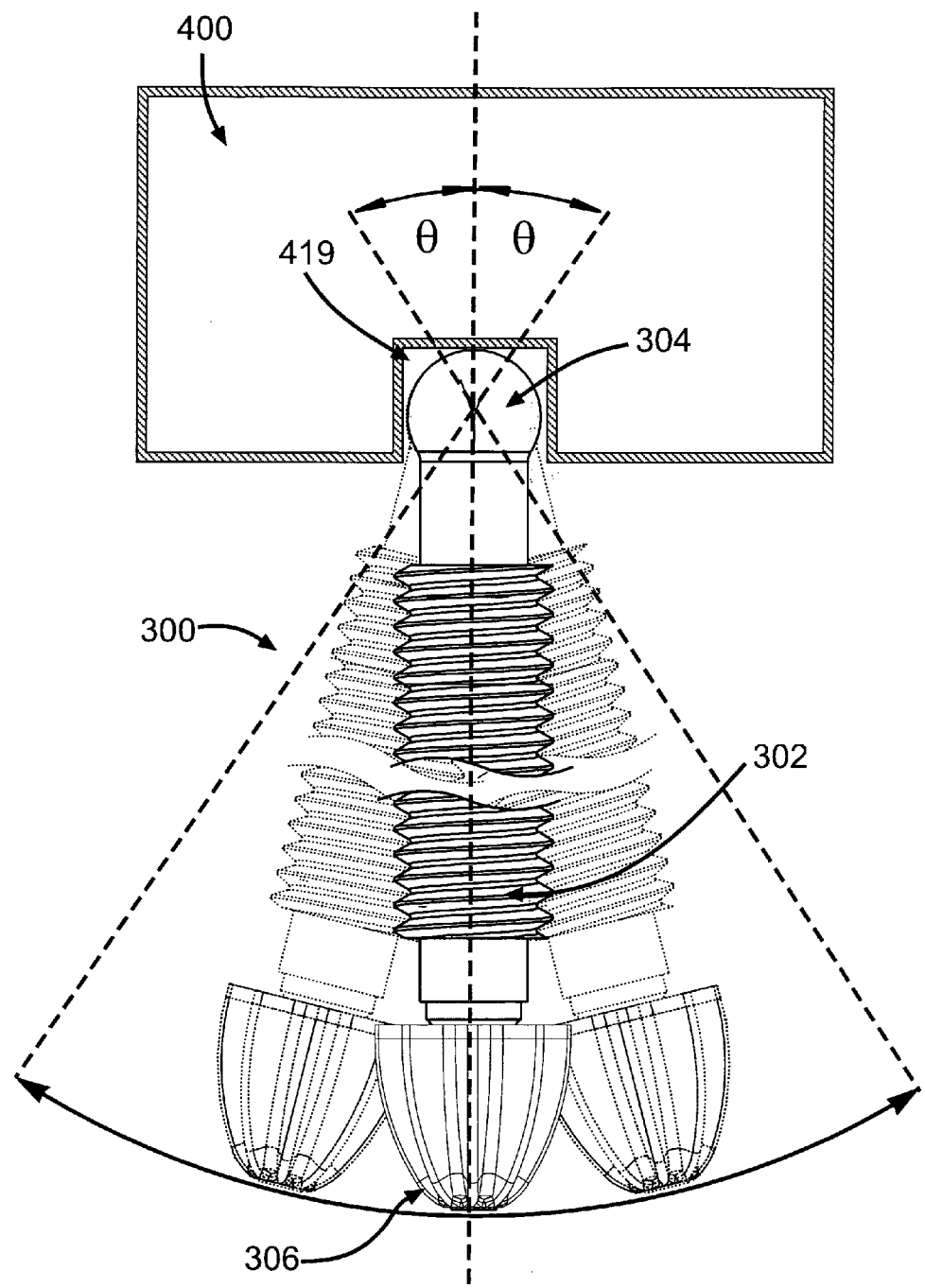
FIG. 8 shows a longitudinal cross-section view of a plunger and a drive screw articulated with a socket located within a plunger, according to some embodiments.
Figure 9C:
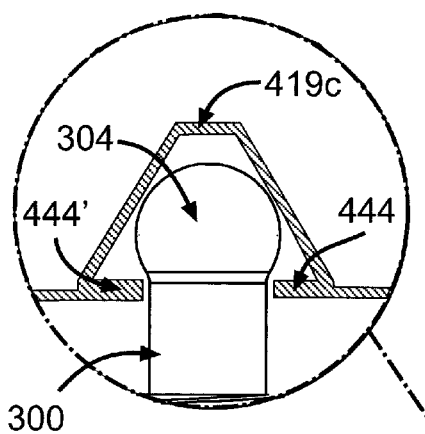
FIGS. 9a-9e show longitudinal cross-section views of a drive screw articulated with various socket configurations of a plunger, according to some embodiments.
Figure 9B:
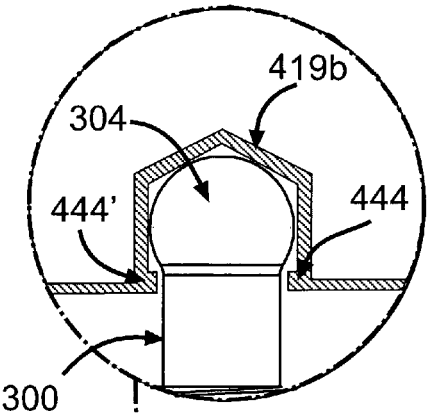
Figure 9D:
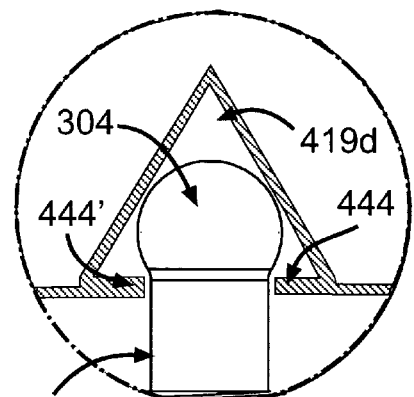
Figure 9A:
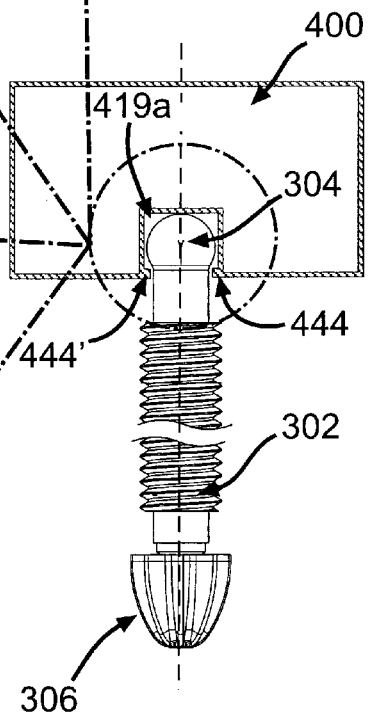
Figure 9E:
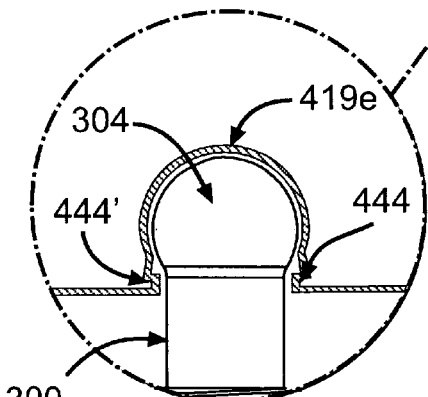

FIG. 8 shows a longitudinal cross-sectional view of an embodiment of the plunger 400 and the drive screw 300 assembly. The drive screw 300 comprises a shaft 302, a proximal end 306, and a distal end 304, according to some embodiments. The plunger 400 may include a socket 419 having an indentation for receiving the distal end 304 of the drive screw 300. As shown in FIG. 8, the drive screw 300 may be articulated with the plunger 400 as a result of the distal end 304 being received by and engaged with the socket 419. Articulation of the distal end 304 within the socket 419 provides for angular movement of the drive screw 300 relative to the plunger 400, in at least one plane. As a result, unintentional lateral movement of the drive screw 300 due to eccentricity or misalignment of the proximal end 306 within the rotating sleeve 114 is absorbed by the articulation between the distal end 304 and the socket 419 and not transferred to the plunger. Accordingly, wobbling of the plunger 400 and inaccuracies in fluid delivery resulting therefrom are prevented.

FIGS. 9a-9e show various embodiments of the socket 419 configured to prevent the plunger 400 from wobbling during forward motion of the plunger 400 within the reservoir 220. The configuration of the socket 419 may vary depending on the embodiment. In some embodiments, the longitudinal cross-section of the socket 419 may be, but is not limited to, quadrangular 419a (see FIG. 9a), pentagonal 419b (see FIG. 9b), trapezoidal 419c (see FIG. 9c), triangular 419d (see FIG. 9d), or circular 419e (see FIG. 9e), or a combination thereof (e.g., quadrangular with a distal circular end). In some embodiments, the transverse cross-section of the socket 419 may be, but is not limited to, circular (e.g., a cylindrical socket, a conical socket or a semispherical socket), in which case, when a spherical distal end is employed, the contact area between the distal end 304 and the socket 419 may be annular. In some embodiments, the transverse cross-section of the socket 419 may be, but is not limited to, polygonal (e.g., a pyramidal socket), in which case, when a spherical distal end is employed, the contact area between the distal end 304 and the socket 419 may be a plurality of points. Some embodiments of the socket 419 may have a transverse cross-section that is partially circular and partially polygonal. In some embodiments, the socket 419 may have one or more protrusions (e.g., latches, an annular protrusion) 444 and 444' to secure the distal end 304 within the socket 419 via a snap-fit arrangement to ensure a reliable coupling therebetween. The snap-fit arrangement may further enable two-way displacement of the plunger 400 within the reservoir 220 upon pulling or pushing of the drive screw 300 (e.g., during the process of filling the reservoir 220). In some embodiments, the one or more protrusions 444 and 444' may be flexible (i.e., fabricated from a substantially resilient material), at least in part, to enable coupling the distal end 304 with the socket 419 by forcefully pushing the distal end 304 inwardly into the socket 419 past the one or more protrusions 444 and 444', e.g., in the nature of a snap-fit engagement. Once the distal end 304 is positioned within the socket 419, the one or more protrusions 444 and 444' secure the distal end 304 within the socket 419 and prevent disconnection of the drive screw 300 from the plunger 400 (e.g., upon pulling the drive screw 300 during the process of filling the reservoir 220).

Figure 10:
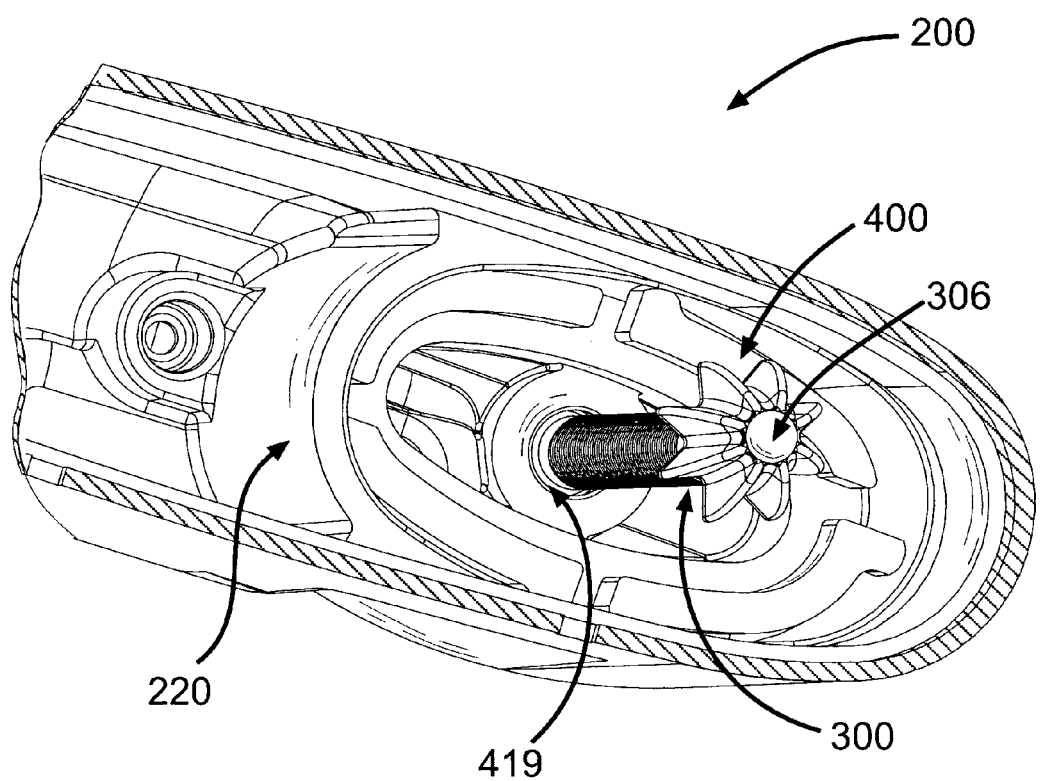
FIG. 10 shows a partial view of a disposable part of a two-piece dispensing unit containing a plunger within a reservoir and a drive screw articulated with the plunger, according to some embodiments.

FIG. 10 shows a partial view of the disposable part 200 with the reservoir 220 according to some embodiments. The drive screw 300 is also shown in FIG. 10 as having a proximal end 306 and being articulated with the socket 419 of the plunger 400.

FIGS. 11a-11b show a longitudinal cross-sectional view of the disposable part 200, according to some embodiments. The plunger 400 may be movable within the reservoir 220 and contain a gasket 420 and a socket 419 according to some embodiments. The location of the socket 419 and/or its depth within the plunger 400 may vary depending on the embodiment. As shown in FIGS. 11a-11b, the socket 419 may be configured to be located at the distal end of the plunger 400, preferably further than the gasket 420 (i.e., deeper within the plunger 400 than the location of the groove 408 supporting the gasket 420), such that the distal end 304 of the drive screw 300 precedes the gasket 420 when the plunger 400 is advanced within the reservoir 220. As a result, the drive screw 300 effectively pulls the plunger 400 rather than pushes the plunger 400, which further stabilizes the plunger 400 within the reservoir 220 and prevents wobbling of the plunger 400. If the plunger 400 includes more than one gasket, the socket 419 may be located further (or deeper) than the most distal gasket (e.g., further than the gasket supported by groove 501 in FIG. 5a). The drive screw 300 may include a shaft 302, a proximal end 306 and a distal end 304 articulated with the socket 419. Upon rotation of the rotating sleeve 114 (not shown), the drive screw 300 is rotated via engagement of the proximal end 306 with the rotating sleeve 114. Rotation of the shaft 302 within the drive nut 209 (held stationary with the disposable part 200) causes linear displacement of the drive screw 300 and, in turn linear displacement of the plunger 400 within the reservoir 220.

Any and all publications or other documents, including but not limited to, patents, patent applications, articles, webpages or books referred to in the present application, are herein incorporated by reference in their entirety.

Although particular embodiments have been disclosed herein in detail, this has been done by way of example for purposes of illustration only, and is not intended to be limiting with respect to the scope of the appended claims. In particular, it is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the disclosures described herein. Other, unclaimed disclosures are also contemplated. The inventors reserve the right to pursue such disclosures in later claims.

What is claimed is:

1. A portable pump device for delivering fluid into the body of a user, the device comprising:
   a first part comprising a motor, one or more gears and a receiving portion driven by at least one of the motor and the one or more gears; and
   a second part configured to connect removably with the first part, the second part comprising a reservoir, a plunger having an unthreaded socket, and a drive screw having a proximal end and a distal end, the distal end of the drive screw being received at least partially in the socket of the plunger so as to be articulated with the plunger and axially retained by the socket of the plunger so as to move the plunger synchronized therewith in both axial directions, and the proximal end of the drive screw being configured to directly contact and removably engage the receiving portion of the first part upon connection of the first part and the second part, wherein rotation of the drive screw by the receiving portion displaces the plunger in a linear direction within the reservoir without rotating the plunger, and wherein the second part further comprises an engagement member having a threaded portion and a non-threaded portion, the engagement member being configured to be movable between at least a first position in which the non-threaded portion of the engagement member allows the drive screw to move linearly substantially unrestricted and a second position in which the drive screw is coupled to the threaded portion of the engagement such that the rotation of the drive screw by the receiving portion displaces the plunger in the linear direction within the reservoir, wherein the plunger has:
- a first groove which has a uniform depth and is configured such that an entire outer circumference of a gasket supported by the first groove maintains constant contact with an inner wall of the reservoir, and either:
- a second groove which has a non-uniform depth and includes one or more projections such that a second gasket supported by the second groove contacts the inner wall of the reservoir via those portions of the second gasket positioned over the one or more projections, or
- two or more guide flaps that support the plunger within the reservoir, each guide flap having at least a portion that maintains contact with the inner wall of the reservoir as the plunger is advanced within the reservoir, wherein each of the two or more guide flaps extends from the plunger at a single point of contact and are separate from each other in a plane transverse to the axial directions so that positioning and orientation of each guide flap relative to the inner wall of the reservoir is adjustable individually with elasticity.

2. The device according to claim 1, wherein the distal end of the drive screw is spherical in shape.

3. The device according to claim 1, wherein the distal end of the drive screw is truncated.

4. The device according to claim 1, wherein the socket includes a longitudinal cross-section selected from the group consisting of polygonal, circular and a combination thereof and/or includes a transverse cross-section selected from the group consisting of polygonal, circular and a combination thereof.

5. The device according to claim 1, wherein the articulation of the distal end of the drive screw with the socket of the plunger permits an angular movement of the drive screw relative to the plunger.

6. The device according to claim 1, wherein the socket includes one or more protrusions to hold the distal end of the drive screw at least partially in the socket upon engagement of the distal end of the drive screw with the socket.

7. The device according to claim 1, wherein the engagement of the distal end of the drive screw with the socket comprises a snap-fit engagement.

8. The device according to claim 1, wherein articulation of the distal end of the drive screw with the socket is configured to enable pushing of the plunger using the drive screw, pulling of the plunger using the drive screw and substantially unrestricted rotation of the distal end within the socket.

9. The device according to claim 1, wherein the reservoir includes a non-circular cross-section and wherein the cross-section of at least a portion of the plunger corresponds to the non-circular cross-section of the reservoir.

10. The device according to claim 9, wherein the plunger comprises oval shape.

11. The device according to claim 1, wherein at least a portion of a wall of the second part comprises at least a portion of at least one wall of the reservoir.

12. The device according to claim 1, wherein the fluid being delivered comprises insulin.

13. The device according to claim 1, further comprising a cradle unit securable to the skin of the user, wherein one or more of housings of the first part and the second part are removably connectable to the cradle unit.

14. The device according to claim 1, wherein the first part comprises a reusable part including a reusable part housing and wherein the second part comprises a disposable part including a disposable part housing.

15. The device according to claim 1, wherein the engagement member comprises a drive nut.

16. The device according to claim 1, wherein at least a portion of the one or more flaps is resilient.

17. A portable pump device for delivering fluid into the body of a user, the device comprising:
- a first part comprising a motor, one or more gears and a receiving portion driven by at least one of the motor and the one or more gears; and
- a second part configured to connect removably with the first part, the second part comprises:
  - a reservoir for retaining the fluid;
  - a plunger having a socket; and
  - a drive screw having a proximate end and a distal end, the proximal end of the drive screw being configured to directly contact and removably engage the receiving portion of the first part upon connection of the first part and the second part, and the distal end being received at least partially in the socket of the plunger so as to be articulated with the plunger and be axially retained by the socket of the plunger so as to move the plunger synchronized therewith in both axial directions, the distal end of the drive screw and the socket of the plunger being configured and arranged such that rotation of the drive screw displaces the plunger in a linear direction within the reservoir without substantially rotating the plunger;
  - wherein the distal end of the drive screw has a spherical shape and the socket has a polygonal shape,
  - wherein the socket is non-threaded,
  - wherein the distal end of the drive screw and the socket engage by a snap-fit engagement, and
  - wherein the plunger has two or more guide flaps that support the plunger within the reservoir, each guide flap having at least a portion that maintains contact with the inner wall of the reservoir as the plunger is advanced within the reservoir, wherein each of the two or more guide flaps extends from the plunger at a single point of contact and are separate from each other in a plane transverse to the axial directions so that positioning and orientation of each guide flap relative to the inner wall of the reservoir is adjustable individually with elasticity.

18. A portable pump device for delivering fluid into the body of a user, the device comprising:
- a first part comprising a motor, one or more gears and a receiving portion driven by at least one of the motor and the one or more gears; and
- a second part configured to connect removably with the first part, the second part comprises:
  - a reservoir for retaining the fluid;
  - a plunger; and
  - a drive screw having a proximate end and a distal end, the proximal end of the drive screw being configured to directly contact and removably engage the receiving portion of the first part upon connection of the first part and the second part, and the distal end being articulated with the plunger,
- wherein rotation of the drive screw displaces the plunger in a linear direction within the reservoir without substantially rotating the plunger,
- wherein the plunger includes a socket for engagement of the distal end of the drive screw to provide articulation therebetween, such that the articulation of the distal end of the drive screw with the socket of the plunger permits an angular movement of the drive screw relative to the plunger, and axially retain the distal end of the drive screw by the socket so as to move the plunger synchronized therewith in both axial directions,
- wherein the socket is non-threaded,
- wherein the distal end of the drive screw and the socket engage by a snap-fit engagement, and
- wherein the plunger has:
  - a first groove which has a uniform depth and is configured such that an entire outer circumference of a gasket supported by the first groove maintains constant contact with an inner wall of the reservoir, and either:
    - a second groove which has a non-uniform depth and includes one or more projections such that a second gasket supported by the second groove contacts the inner wall of the reservoir via those portions of the second gasket positioned over the one or more projections, or
    - two or more guide flaps that support the plunger within the reservoir, each guide flap having at least a portion that maintains contact with the inner wall of the reservoir as the plunger is advanced within the reservoir, wherein each of the two or more guide flaps extends from the plunger at a single point of contact and are separate from each other in a plane transverse to the axial directions so that positioning and orientation of each guide flap relative to the inner wall of the reservoir is adjustable individually with elasticity.

19. The device according to claim 1, wherein the receiving portion is a rotating sleeve and the proximal end of the drive screw is configured to directly contact and removably engage within the rotating sleeve upon connection of the first part and the second part, and rotate when the rotating sleeve is rotated.

20. The device according to claim 19, wherein the drive screw is received at least partially in the socket of the plunger so as to be articulated with the plunger such that unintentional lateral movement of the drive screw due to eccentricity or misalignment of the proximal end within the rotating sleeve is absorbed by articulations between the distal end and the socket and not transferred to the plunger.

21. The device according to claim 1, wherein the proximal end of the drive screw is star-shaped.

* * * * *

UNITED STATES PATENT AND TRADEMARK OFFICE
CERTIFICATE OF CORRECTION

PATENT NO. : 9,999,722 B2
APPLICATION NO. : 13/142912
DATED : June 19, 2018
INVENTOR(S) : Ofer Yodfat Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 740 days.

Signed and Sealed this
Twenty-first Day of May, 2019

Andrei Iancu
*Director of the United States Patent and Trademark Office*